US009592224B2

(12) United States Patent
Martínez Gil et al.

(10) Patent No.: US 9,592,224 B2
(45) Date of Patent: Mar. 14, 2017

(54) SUBSTITUTED BENZOTHIAZOLES AND THERAPEUTIC USES THEREOF FOR THE TREATMENT OF HUMAN DISEASES

(71) Applicant: CONSEJO SUPERIOR DE INVESTIGACIONES CIENTÍFICAS, Madrid (ES)

(72) Inventors: Ana Martínez Gil, Madrid (ES); Daniel Ignacio Pérez Fernández, Madrid (ES); Carmen Gil Ayuso-Gontán, Madrid (ES); Irene García Salado, Madrid (ES); Miriam Redondo Sancho, Madrid (ES); Concepción Pérez Martínez, Madrid (ES)

(73) Assignee: DONSEJO SUPERIOR DE INVESTIGACIONES CIENTÍFICAS (CSIC), Madrid (ES)

(*) Notice: Subject to any disclaimer, the term of this patent is extended or adjusted under 35 U.S.C. 154(b) by 16 days.

(21) Appl. No.: 14/762,360

(22) PCT Filed: Dec. 12, 2013

(86) PCT No.: PCT/ES2013/070874
§ 371 (c)(1),
(2) Date: Jul. 21, 2015

(87) PCT Pub. No.: WO2014/114825
PCT Pub. Date: Jul. 31, 2014

(65) Prior Publication Data
US 2015/0352082 A1 Dec. 10, 2015

(30) Foreign Application Priority Data

Jan. 22, 2013 (ES) .................................. 201330065

(51) Int. Cl.
*A61K 31/425* (2006.01)
*A61K 31/428* (2006.01)
*C07D 277/82* (2006.01)

(52) U.S. Cl.
CPC .......... *A61K 31/428* (2013.01); *C07D 277/82* (2013.01)

(58) Field of Classification Search
CPC ........................... A61K 31/428; C07D 277/82
USPC ....................................................... 514/367
See application file for complete search history.

(56) References Cited

U.S. PATENT DOCUMENTS

| 4,208,419 A | 6/1980 | Paget et al. | |
|---|---|---|---|
| 6,140,330 A * | 10/2000 | Mori | C07D 277/46 514/235.8 |
| 2009/0163545 A1* | 6/2009 | Goldfarb | A61K 31/122 514/312 |

FOREIGN PATENT DOCUMENTS

| GB | 1535223 | 12/1978 |
|---|---|---|
| WO | WO-0157008 | 8/2001 |
| WO | WO-0246173 | 6/2002 |
| WO | WO-2005026137 | 3/2005 |
| WO | WO-2005037845 | 4/2005 |
| WO | WO-2006018662 | 2/2006 |
| WO | WO-2012026491 | 3/2012 |

OTHER PUBLICATIONS

Amnerkar et al,Synthesis, anticonvulsant activity and 3-D-QSAR study of some prop-2-eneamido and 1-acetyl-pyrazolin derivatives of aminobenzothiazole, European Journal of Medicinal Chemistry, 2010, 45(1), p. 149-159.*
Blaettermann et al, A biased ligand forOXE-R uncouples Galpha and Gbetagamma signaling within a heterotrimer, Nature Chemical Biology, 2012, 8(7), p. 631-638 (abstract ) (1 page).*
PCT Search Resort mailed Mar. 7, 2014, PCT/ES2013/070874, 3 pages.
Caputo, R., et al., "Synthesis of benzothiazole derivatives and their biological evaluation as anticancer agents", Med Chem Res 21, 2012 , 2644-2651.
Crivori, P., et al., "Predicting Blood-Brain Barrier Permeation from Three-Dimensional Molecular Structure", *J. Med. Chem.*, vol. 43, (2000), 2204-2216.
Di, L., et al., "High throughput artificial membrane permeability assay for blood-brain barrier", *European Journal of Medicinal Chemistry*, vol. 38, (2003), 223-232.
Osakada, F., et al., "In vitro differentiation of retinal cells from human pluripotent stem cells by small-molecule induction", *Journal of Cell Science*, vol. 122, (2009), 3169-3179.
Perez, D. I., et al., "Protein Kinases CK1 and CK2 as New Targets for Neurodegenerative Diseases", *Medicinal Research Reviews*, vol. 31, No. 6, (2011).
Partial Supplementary European Search Report mailed Jun. 14, 2016, EP Appln. No. 13872316.8, 12 pages.
Azam, Faizul, et al., "Structure-based design, synthesis, and molecular modeling studies of 1-(benzo[d]thiazol-2-yl)-3-(substituted aryl)urea derivatives as novel anti-Parkinsonian agents", *Medicinal Chemistry Research*, vol. 21, No. 9 (2011), 2630-2643.

(Continued)

*Primary Examiner* — T. Victor Oh
(74) *Attorney, Agent, or Firm* — Blakely Sokoloff Taylor & Zafman LLP

(57) ABSTRACT

The invention relates to a family of differently substituted benzothiazoles having inhibitory activity against casein kinase 1 (CK-1) enzyme, as a result of which they are suitable for use in the treatment or prevention of diseases caused by this enzyme, particularly diseases associated with circadian rhythm and inflammatory, autoimmune, psychiatric, neurodegenerative, neurological or ophthalmic diseases, as well as for inducing cell regeneration

19 Claims, No Drawings

(56) References Cited

OTHER PUBLICATIONS

Li, Zheng, et al., "Microwave Promoted Environmentally Benign Synthesis fo 2-Aminobenzothiazoles and Their Urea Derivatives", *Phosphorus, Sulfur, and Silicon and the Related Elements*, vol. 183, No. 5, (2008), 1124-1133.
Salado, I. G., et al., "Protein Kinase CK-1 Inhibitors As New Potential Drugs for Amyotrophic Lateral Sclerosis", Journal of Medicinal Chemistry, vol. 57, No. 6 (2014), 2755-2772.
Song, Eun Y., et al., "Synthesis of amide and urea derivatives of benzothiazole as Raf-1 inhibitor", *European Journal of Medicinal Chemistry* vol. 43, 2008, 1519-1524.
Yabuuchi, Takahiro, et al., "Synthesis of New Antimicrobials III. Synthesis of Chlorine-subsituted 4-Thiocyanatoaniline and 2-Amino-6-chlorobenzothiazole Derivatives", *Chem. Pharm. Bull.*, vol. 23, No. 3, (1975), 659-663.

* cited by examiner

SUBSTITUTED BENZOTHIAZOLES AND THERAPEUTIC USES THEREOF FOR THE TREATMENT OF HUMAN DISEASES

CROSS-REFERENCE TO RELATED APPLICATIONS

The present patent application is a national phase application of International Application No. PCT/ES2013/070874, filed Dec. 12, 2013, which claims priority to Spanish Application No. P201330065, filed Jan. 22, 2013, the disclosures of which are incorporated herein by reference.

SECTOR OF THE ART AND OBJECT OF THE INVENTION

The present invention relates to a family of derivatives of substituted benzothiazoles having inhibitory activity of the enzyme casein kinase 1 (CK-1), due to which they are useful for the treatment and/or prevention of diseases mediated by said enzyme, especially inflammatory, neurological, psychiatric, neurodegenerative and/or ophthalmic diseases and in certain regenerative processes. Therefore, the invention falls within the field of pharmaceutical chemistry and pharmacology.

STATE OF THE ART

CK-1 protein kinase is a serine/threonine kinase which was first characterised in the early 70s. The CK-1 family is formed of seven isoforms CK-1α, CK-1γ1-CK-1γ3, CK-1β, CK-1δ and CK-1ε. All isoforms retain their kinase domain (53%-98%) and differ in the C-terminal region. This kinase family does not require the phosphorylation of their activation loop, while the activity of CK-1δ/ε can be regulated by the autophosphorylation of its C-terminal region in an intramolecular-type reaction. CK-1 is found in different cell types and in many subcellular compartments, such as for example the plasma membrane, cytosol and nucleus. Due to being a widely distributed kinase, it is believed to play an essential role in regulatory processes, being involved in various biological functions such as the regulation of DNA repair, cell morphology, modulation of Wnt/β-catenin metabolic pathway and regulation of circadian rhythms.

In recent years it has been described as a pharmaceutical target of interest for the treatment of various pathologies, including neurodegenerative diseases [Perez, D. I.; Gil, C.; Martinez, A., Protein kinases CK-1 and CK-2 as new targets for neurodegenerative diseases. *Med Res Rev* 2011, 31 (6), 924-54] and neurological diseases, and their effect on circadian rhythm. There are also data which suggest that CK-1 is a good pharmacological target in chronic inflammatory processes as well as regenerative processes of the central nervous system and retina stem cells.

It has been shown that overexpression or excessive activation of CK-1, is related to many degenerative diseases, also including sleep disorders, inflammation and cancer. The CK-1 protein kinase phosphorylates certain proteins such as TDP-43 or tau, resulting in post-transductional changes and abnormal protein inclusions.

Amyotrophic Lateral Sclerosis (ALS) is a degenerative muscle disease that triggers the functional decline of motor neurons and death, causing progressive muscle paralysis. There is currently no effective treatment for ALS, Riluzole being (Rilutek®) the only drug approved for its treatment, which moderately slows the progression of the disease. Sporadic ALS type represents 90%-95% of cases of the disease. Both in sporadic and familial ALS, it has recently been discovered that TDP-43 protein is hyperphosphorylated in patients' brains. One of the proteins involved in the phosphorylation of TDP-43 is CK-1 enzyme. Therefore, the search for CK-1 inhibitors represents a novel therapeutic target for the treatment of this disease.

Alzheimer's disease (AD) is a neurodegenerative disease characterised in its typical form by an immediate loss of memory and other mental abilities, as nerve cells die and different areas of the brain atrophies. In Alzheimer's patients' brains, an abnormal increase in beta-amyloid and tau proteins has been observed. The so-called tau hypothesis argues that hyperphosphorylation of tau protein initiates the cascade of disorders inherent to Alzheimer's disease. CK-1 enzyme is considered as one of the enzymes involved in the phosphorylation of tau protein.

CK-1 enzyme is also related to inflammatory, neurological, psychiatric and/or ophthalmic diseases and in certain regenerative processes [Fumitaka, O.; Zi-Bing, J.; Yasuhiko, H.; Hanako, I.; Teruko, D.; Kiichi, W.; Yoshiki, S.; Masayo, T. In vitro differentiation of retinal cells from human pluripotent stem cells by small-molecule induction. *J. Cell Sci.* 2009, 122, 3169-3179].

CK-1 inhibitors with good pharmacological properties and good safety profiles can be effective drugs for treating various currently incurable human pathologies. WO2005026137 discloses a broad family of inhibitors with a benzothiazole-benzylamides structure which act as modulators of ABC transporters of cell membranes for the treatment of neurodegenerative diseases such as Parkinson's disease, Alzheimer's disease and Amyotrophic Lateral Sclerosis. The benzothiazole-benzylamides described herein differ from those described in WO2005026137 in that, besides having different substituents, they do not have any stereogenic centre and, therefore, do not give rise to racemic mixtures. This fact considerably simplifies the process of evaluation of a potential drug through the clinical phases to which they are subjected and must fulfil before being placed on the market. This is because the inactive enantiomer must be equally evaluated to demonstrate that it is not harmful to health.

The presence of a stereogenic centre at the position located on the carbon acetoamide of benzothiazole-benzylamide structures seems to indicate that said stereogenic centre may be essential to achieving the required activity, as WO2002046173 discloses a similar family to that disclosed in WO2005026137, with similar substitution at that position, whose compounds act as glucokinase enzyme activators used in the treatment of type 2 diabetes. However, the compounds of the present invention lack such stereogenic centre and, therefore, have greater structural simplicity which facilitates their synthesis and avoids problems, such as for example toxicity, that may arise in the use of racemic mixtures of active compounds against a certain disease when conducting clinical phases of development of said compound, as mentioned in the preceding paragraph.

WO2012026491 discloses a family of benzothiazole-benzylamides for the treatment of cardiovascular diseases by myocardial cell differentiation.

Due to the need for new molecules to combat diseases for which there are no existing treatments or existing treatments can be improved, the present invention provides a group of compounds that are inhibitors of CK-1 enzyme, which is an enzyme associated with a large number of inflammatory diseases, particularly neurological, psychiatric, neurodegenerative and/or ophthalmic diseases, and in certain regenerative processes, and which are an alternative to existing drugs.

DETAILED DESCRIPTION OF THE INVENTION

The authors of the present invention have developed a family of benzothiazole-benzylamides with greater activity than those described in the prior art and having the additional advantage over such compounds of not giving rise to racemic mixtures, on not having stereogenic centres.

In a first aspect, the present invention relates to the use of a compound having the following formula (I):

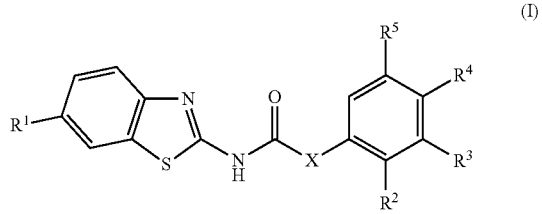

its pharmaceutically acceptable salts, tautomers and/or solvates, wherein
X is selected from among NH, $CH_2$, CHPh, $CH_2CH_2$, $CH_2CHPh$, CH=CH, $CH_2OCH_2$, $CH_2NHCO$, $CH_2NHCOCHPh$ and $CH_2NHCOCH_2$.
$R^1$ is selected from among $R^6$, halogen, $CF_3$, $OCF_3$, $OR^6$, $CO_2R^6$, $SO_2N(R^6)_2$ and $NO_2$.
$R^2$, $R^3$, $R^4$ and $R^5$ are independently selected from among H, halogen, O-alkyl ($C_1$-$C_5$) and $NH_2$, $NHR^6$, CN, $NO_2$, $OCF_3$, $CO_2R^6$.
$R^6$ is selected from among H and alkyl ($C_1$-$C_5$).
provided that when X is CHPh, $CH_2CHPh$ or $CH_2NHCOCHPh$, then $R^2$, $R^3$, $R^4$ and $R^5$ are H;
and provided that the compound N-(6-ethoxy-benzothiazole-2-yl)-2-(4-chlorophenyl)acetamide is excluded from the formula (I),
for manufacturing a drug for the treatment and/or prevention of a disease mediated by casein kinase 1 (CK-1) enzyme.

The term "alkyl" refers, in the present invention, to radical linear or branched hydrocarbon chains having 1 to 5 carbon atoms, and which bind to the rest of the molecule by a single bond, for example, methyl, ethyl, n-propyl, i-propyl, n-butyl, terc-butyl, sec-butyl, n-pentyl, etc. The alkyl groups may be optionally substituted by one or more substituents such as halogen, hydroxyl, alkoxyl, carboxyl, carbonyl, cyano, acyl, alkoxycarbonyl, amino, nitro, mercapto and alkylthio. The term "halogen" refers to fluoride (—F), chloride (—Cl), bromide (Br) or iodine (—I).

"Ph" stands for phenyl.

The compounds of the present invention represented by the general formula (I) may include isomers, depending on the presence of multiple bonds (for example Z, E).

Unless otherwise stated, the compounds used in the invention are intended to include compounds that differ only in the presence of one or more isotopically enriched atoms. For example, compounds having the present structures except for the substitution of a hydrogen atom for a deuterium atom or a tritium atom, or the substitution of a carbon atom for a carbon atom enriched in $^{13}C$ or $^{14}C$ or a nitrogen atom enriched in $^{15}N$ fall within the scope of this invention.

The term "pharmaceutically acceptable salts or solvates thereof" relates to salts or solvates which, on being administered to the recipient, are capable of providing a compound such as that described herein. The preparation of salts and derivatives can be carried out by methods known in the state of the art. Preferably, "pharmaceutically acceptable" relates to molecular entities and compositions that are physiologically tolerable and do not typically produce an allergic reaction or a similar unfavourable reaction, such as gastric upset, dizziness and similar side effects, when administered to a human. Preferably, the term "pharmaceutically acceptable" means approved by a regulatory agency of a federal or state government or collected in the US Pharmacopoeia or other generally recognised pharmacopeia for use in animals and, more particularly, in humans.

For example, pharmaceutically acceptable salts of the compounds previously described herein are synthesised from the previously described compound containing a basic or acidic moiety by conventional chemical methods. In general, such salts are prepared, for example, by reacting the free acid or basic forms of these compounds with a stoichiometric quantity of the appropriate base or acid in water or in an organic solvent or a mixture of both. Generally, non-aqueous media like ether, ethyl acetate, ethanol, isopropanol or acetonitrile are preferred. Examples of acid addition salts include addition salts of mineral acids such as, for example, hydrochloride, hydrobromide, hydroiodide, sulfate, nitrate, phosphate and addition salts of organic acids such as, for example, acetate, maleate, fumarate, citrate, oxalate, succinate, tartrate, malate, mandelate, methanesulfonate and p-toluenesulfonate. Examples of alkali addition salts include inorganic salts such as, for example, sodium, potassium, calcium, ammonium, magnesium, aluminium and lithium, and organic alkaline salts such as, for example, ethylenediamine, ethanolamine, N-dialkylenethanolamine, glucamine and basic amino acid salts.

The compounds used in the invention may be in crystalline form, either as free compounds or as solvates (e.g.: hydrates), and it is understood that both forms fall within the scope of the present invention. Solvation methods are generally known in the state of the art. Suitable solvates are pharmaceutically acceptable solvates. In a particular embodiment, the solvate is a hydrate.

"Tautomers" are understood to be the two isomers that differ only in the position of a functional group because between the two forms there is a chemical balance in which a migration of a group or atom occurs.

The present invention also relates to a compound of formula (I) as defined above for use in the treatment and/or prevention of a disease mediated by CK-1 enzyme.

The present invention equally relates to a method for the prevention or treatment of a disease mediated by CK-1 enzyme which comprises administering, to a patient in need thereof, a therapeutically effective quantity of a compound of formula (I) as previously defined.

The term "therapeutically effective quantity" means the necessary quantity of a compound for the treatment or prevention of the disease, disorder or condition to be effective.

In a preferred embodiment of the present invention $R^2$, $R^3$, $R^4$ and $R^5$ are independently selected from among H, halogen and O-alkyl ($C_1$-$C_5$).

In another more preferred embodiment of the present invention, X is $CH_2$, $CH_2CH_2$, CHPh or NH.

In another even more preferred embodiment of the present invention, X is $CH_2$.

In another preferred embodiment of the present invention, $R^1$ is $CF_3$, halogen or alkyl.

In another more preferred embodiment of the present invention, $R^1$ is $CF_3$ or halogen.

In another more preferred embodiment of the present invention, $R^1$ is $CF_3$.

In another much more preferred embodiment of the present invention, X is $CH_2$ and $R^1$ is $CF_3$.

In a more preferred embodiment, the compound of formula (I) is selected from the following group:
N-(6-trifluoromethylbenzothiazole-2-yl)-2-(4-chlorophenyl)acetamide
N-(6-chlorobenzothiazole-2-yl)-2-(4-methoxyphenyl)acetamide
N-(6-trifluoromethylbenzothiazole-2-yl)-2-(4-methoxyphenyl)acetamide
N-(6-trifluoromethylbenzothiazole-2-yl)-2-(3-chlorophenyl)acetamide
N-(6-methylbenzothiazole-2-yl)-2-(3-chlorophenyl)acetamide
N-(6-trifluoromethylbenzothiazole-2-yl)-2-(3-methoxyphenyl)acetamide
N-(6-trifluoromethylbenzothiazole-2-yl)-2-(2-chlorophenyl)acetamide
N-(6-trifluoromethylbenzothiazole-2-yl)-2-(2-methoxyphenyl)acetamide
N-(6-trifluoromethylbenzothiazole-2-yl)-2-(3,4-dichlorophenyl)acetamide
N-(¾-trifluoromethylbenzothiazole-2-yl)-2-(3,4,5-trimethoxyphenyl)acetamide
N-(6-trifluoromethoxybenzothiazole-2-yl)-2-(3,4,5-trimethoxyphenyl)acetamide
N-(6-trifluoromethylbenzothiazole-2-yl)-2-phenylacetamide
N-(6-trifluoromethylbenzothiazole-2-yl)-2-(3-(trifluoromethyl)-phenyl)acetamide
N-(benzothiazole-2-yl)-2-phenylacetamide
N-(6-trifluoromethylbenzothiazole-2-yl)-2,2-diphenylacetamide
N-(6-methoxybenzothiazole-2-yl)-2,2-diphenylacetamide
N-(6-nitrobenzothiazole-2-yl)-3-phenylpropanamide
N-(benzothiazole-2-yl)-2-(4-fluorophenyl)acetamide
N-(6-methoxybenzothiazole-2-yl)-2-(4-methoxyphenyl)acetamide
N-(benzothiazole-2-yl)-2-(3-chlorophenyl)acetamide
N-(6-methoxybenzothiazole-2-yl)-2-(4-chlorophenyl)acetamide
N-(6-methoxybenzothiazole-2-yl)-2-(3-chlorophenyl)acetamide
N-(6-trifluoromethoxybenzothiazole-2-yl)-2-(3-chlorophenyl)acetamide
N-(6-trifluoromethylbenzothiazole-2-yl)-N'-(3-chlorophenyl)urea
N-(6-methoxybenzothiazole-2-yl)-2-(3,4-dichlorophenyl)acetamide
N-(6-ethoxybenzothiazole-2-yl)-2-(3-methoxyphenyl)acetamide
N-(6-trifluoromethoxybenzothiazole-2-yl)-2-(2-methoxyphenyl)acetamide
N-(6-trifluoromethoxybenzothiazole-2-yl)-2-(3,4-dichlorophenyl)acetamide
N-(6-trifluoromethylbenzothiazole-2-yl)-2-(2,5-dimethoxyphenyl)acetamide
N-(6-methylbenzothiazole-2-yl)-2-(2-methoxyphenyl)acetamide
N-(6-chlorobenzothiazole-2-yl)-2-(2-methoxyphenyl)acetamide
N-(6-bromobenzothiazole-2-yl)-2-(2-methoxyphenyl)acetamide
and its pharmaceutically acceptable salts, solvates or tautomers.

In an even more preferred embodiment the compound of formula (I) is selected from the following group:
N-(6-trifluoromethylbenzothiazole-2-yl)-2-(4-chlorophenyl)acetamide
N-(6-chlorobenzothiazole-2-yl)-2-(4-methoxyphenyl)acetamide
N-(6-trifluoromethylbenzothiazole-2-yl)-2-(4-methoxyphenyl)acetamide
N-(6-trifluoromethylbenzothiazole-2-yl)-2-(3-chlorophenyl)acetamide
N-(6-methylbenzothiazole-2-yl)-2-(3-chlorophenyl)acetamide
N-(6-trifluoromethylbenzothiazole-2-yl)-2-(3-methoxyphenyl)acetamide
N-(6-trifluoromethylbenzothiazole-2-yl)-2-(2-chlorophenyl)acetamide
N-(6-trifluoromethylbenzothiazole-2-yl)-2-(2-methoxyphenyl)acetamide
N-(6-trifluoromethylbenzothiazole-2-yl)-2-(3,4-dichlorophenyl)acetamide
N-(6-trifluoromethylbenzothiazole-2-yl)-2-(3,4,5-trimethoxyphenyl)acetamide
N-(6-trifluoromethoxybenzothiazole-2-yl)-2-(3,4,5-trimethoxyphenyl)acetamide
N-(6-trifluoromethylbenzothiazole-2-yl)-2-phenylacetamide
N-(6-trifluoromethylbenzothiazole-2-yl)-2-(3-(trifluoromethyl)phenyl)acetamide
and its pharmaceutically acceptable salts, solvates or tautomers.

In an even more preferred embodiment, the compound of formula (1) is selected from the following group:
N-(6-chlorobenzothiazole-2-yl)-2-(4-methoxyphenyl)acetamide
N-(6-trifluoromethylbenzothiazole-2-yl)-2-(4-chlorophenyl)acetamide
N-(6-trifluoromethylbenzothiazole-2-yl)-2-(4-methoxyphenyl)acetamide
N-(6-trifluoromethylbenzothiazole-2-yl)-2-(3-chlorophenyl)acetamide
N-(6-trifluoromethylbenzothiazole-2-yl)-2-(3-methoxyphenyl)acetamide
N-(6-trifluoromethylbenzothiazole-2-yl)-2-(2-methoxyphenyl)acetamide
N-(6-trifluoromethylbenzothiazole-2-yl)-2-(3,4,5-trimethoxyphenyl)acetamide
N-(6-trifluoromethylbenzothiazole-2-yl)-2-phenylacetamide
and its pharmaceutically accepted salts, solvates or tautomers.

The compounds of general formula (I) of the present invention are CK-1 enzyme inhibitors. In a preferred embodiment, CK-1 enzyme is selected from among delta CK-1 (CK-1δ) and CK-1 epsilon (CK-1ε). Therefore, these compounds may be useful for preparing medicines for the treatment and/or prevention of diseases related to the circadian rhythm, such as for example: rapid time zone change syndrome (transoceanic syndrome), night shift worker sleep disorder, delayed sleep phase syndrome and advanced sleep phase disorder.

In another aspect of the present invention, compounds of general formula (I), as CK-1 enzyme inhibitors, can be useful for preparing drugs for the treatment and/or prevention of inflammatory and autoimmune diseases, such as for example: Crohn's disease, ulcerative colitis, multiple sclerosis, encephalitis, myelitis and encephalomyelitis, vasculitis, arthritis, atherosclerosis, osteoarthritis and rheumatoid arthritis.

In another aspect of the present invention, compounds of general formula (I), as CK-1 inhibitors, can be useful for preparing drugs for the treatment and/or prevention of neurological diseases, such as acute neurological disorder, bipolar disorder and conduct disorder, anxiety and depression.

In another particular embodiment, the disease mediated by CK-1 is a neurological disorder selected from among: depression and/or bipolar disorder.

In another aspect of the present invention, compounds of general formula (I), as CK-1 enzyme inhibitors, may be useful for preparing drugs which induce cell regeneration from the proliferation and differentiation of adult stem cells present in the nervous system, hematopoietic system, skeletal system, in the myocardium or in the retina.

In another particular embodiment, the cell regeneration mediated by CK-1 is retinal cell regeneration.

In another aspect of the present invention, compounds of general formula (I), as CK-1 enzyme inhibitors, may be useful for preparing drugs for the treatment of ophthalmic diseases such as, for example, glaucoma, macular degeneration and retinitis pigmentosa.

In another particular embodiment, the ophthalmic disease mediated by CK-1 is retinitis pigmentosa.

In another aspect of the present invention, compounds of general formula (I), as CK-1 enzyme inhibitors, can be useful for preparing drugs for the treatment and/or prevention of diseases that progress with protein post-translational modifications, such as hyperphosphorylation of tau protein, TDP-43, synuclein, hungtintina, etc., such as for example: Alzheimer's disease, postencephalitic Parkinsonism, Tourette syndrome, periodic limb movement pathologies, restless legs syndrome, Huntington's disease, progressive supranuclear palsy, Pick's disease, frontotemporal dementia, amyotrophic lateral sclerosis and muscular dystrophies such as Duchenne muscular dystrophy, myotonic dystrophy and distal muscular dystrophy; cerebral palsy; Friedreich's ataxia, congenital myasthenic syndrome and myasthenia gravis.

In another particular embodiment, the disease that progresses with hyperphosphorilation of tau protein mediated by CK-1 enzyme is Alzheimer's disease and frontotemporal dementia.

In another particular embodiment, the disease that progresses with hyperphosphorilation of synuclein protein mediated by CK-1 enzyme is Parkinson's disease.

In another particular embodiment, the disease that progresses with hyperphosphorilation of TDP-43 protein mediated by CK-1 enzyme is Amyotrophic Lateral Sclerosis (ALS) and frontotemporal dementia.

Another aspect of the invention relates to a compound of formula (I'):

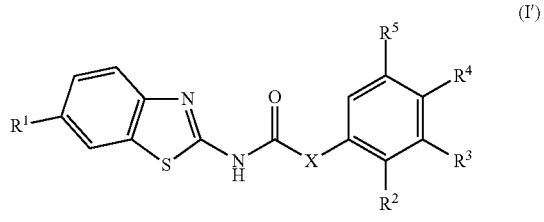

its pharmaceutically acceptable salts, tautomers and/or solvates, wherein
X is selected from among NH, $CH_2$, CHPh, $CH_2CH_2$, $CH_2CHPh$, CH=CH, $CH_2OCH_2$, $CH_2NHCO$, $CH_2NHCOCHPh$ and $CH_2NHCOCH_2$.
$R^1$ is selected from among $R^6$, halogen, $CF_3$, $OCF_3$, $OR^6$, $CO_2R^6$, $SO_2N(R^6)_2$ and $NO_2$.
$R^2$, $R^3$, $R^4$ and $R^5$ are independently selected from among H, halogen and O-alkyl ($C_1$-$C_5$).
$R^6$ is selected from among H and alkyl ($C_1$-$C_5$)
provided that:
when X is CHPh, $CH_2CHPh$ or $CH_2NHCOCHPh$, then $R^2$, $R^3$, $R^4$ and $R^5$ are H;
$R^5$ is O-alkyl ($C_1$-$C_5$) when $R^3$ and $R^4$ are both O-alkyl ($C_1$-$C_5$).
and provided that the following compounds are excluded:
N-(6-(methylsulfonyl)benzothiazole-2-yl)-2-(thiophen-2-yl)acetamide
N-(6-(N,N-diethylsulfamoyl)benzothiazole-2-yl)-2,2-diphenylacetamide
N-(6-sulfamoylbenzothiazole-2-yl)-2,2-diphenylacetamide
N-(6-(N-butylsulfamoyl)benzothiazole-2-yl)-2,2-diphenylacetamide
N-(6-(N-ethylsulfamoyl)benzothiazole-2-yl)-2,2-diphenylacetamide
N-(6-nitrobenzothiazole-2-yl)-3-phenylpropanamide
N-(benzothiazole-2-yl)-2-(4-fluorophenyl)acetamide
N-(6-chlorobenzothiazole-2-yl)-2-(4-methoxyphenyl)acetamide
Carboxylate[2-(2,2-diphenylacetamide)benzothiazole-6-yl]ethyl
(E)-N-(benzothiazole-2-yl)-3-(2,4-dimethoxyphenyl)acrylamide
N-(benzothiazole-2-yl)-2,2-diphenylacetamide
N-(benzothiazole-2-yl)-3,3-diphenylpropanamide
N-(benzothiazole-2-yl)-2-phenylacetamide
N-(benzothiazole-2-yl)-3-(3-chlorophenyl)propanamide
N-(6-ethoxybenzothiazole-2-yl)-2-(3-chlorophenyl)acetamide
N-(6-methoxybenzothiazole-2-yl)-2-(3-methoxyphenyl)acetamide
N-(6-ethoxybenzothiazole-2-yl)-2-(3-methoxyphenyl)acetamide
N-(6-methoxybenzothiazole-2-yl)-2-(4-methoxyphenyl)acetamide
N-(6-ethoxybenzothiazole-2-yl)-2-(4-methoxyphenyl)acetamide
N-(6-methoxybenzothiazole-2-yl)-2-(4-chlorophenyl)acetamide
N-(6-ethoxybenzothiazole-2-yl)-2-(4-chlorophenyl)acetamide
N-(6-methoxybenzothiazole-2-yl)-2-(4-chlorophenyl)acetamide
N-(6-methoxybenzothiazole-2-yl)-2-(2-methoxyphenyl)acetamide
N-(6-methoxybenzothiazole-2-yl)-2-(2-chlorophenyl)acetamide
N-(6-ethoxybenzothiazole-2-yl)-2-(2-chlorophenyl)acetamide
N-(6-methoxybenzothiazole-2-yl)-2-(2-methoxyphenyl)acetamide
N-(6-ethoxybenzothiazole-2-yl)-2-(2-methoxyphenyl)acetamide
N-(6-methoxybenzothiazole-2-yl)-2,2-diphenylacetamide
N-(6-ethoxybenzothiazole-2-yl)-2,2-diphenylacetamide
N-(6-methoxybenzothiazole-2-yl)-2-(3,4,5-trimethoxyphenyl)acetamide N-(6-ethoxybenzothiazole-2-yl)-2-(3,4,5-trimethoxyphenyl)acetamide
N-(6-ethoxybenzothiazole-2-yl)-2-(3,4-dichlorophenyl)acetamide
N-(6-(trifluoromethoxy)benzothiazole-2-yl)-2-(2-methoxyphenyl)acetamide
N-(6-fluorobenzothiazole-2-yl)-2-(2-methoxyphenyl)acetamide
N-(6-chlorobenzothiazole-2-yl)-2-(2-methoxyphenyl)acetamide
N-(6-bromobenzothiazole-2-yl)-2-(2-methoxyphenyl)acetamide
N-(6-methylbenzothiazole-2-yl)-2-(3-chlorophenyl)acetamide
N-[2-(benzothiazole-2-ylamine)-2-oxoethyl]benzamide
N-(benzothiazole-2-yl)-2-(2-phenylacetamide)acetamide
N-(6-chlorobenzothiazole-2-yl)-2-(2,5-dimethoxyphenyl)acetamide
N-(6-methoxybenzothiazole-2-yl)-2-(2,5-dimethoxyphenyl)acetamide In a preferred embodiment of the present invention, X is $CH_2$, $CH_2CH_2$, CHPh or NH.

In a more preferred embodiment of the present invention, X is $CH_2$.

In another preferred embodiment of the present invention, $R^1$ is $CF_3$, halogen or alkyl.

In another more preferred embodiment of the present invention, $R^1$ is $CF_3$ or halogen.

In another more preferred embodiment of the present invention, $R^1$ is $CF_3$.

In another much more preferred embodiment of the present invention, X is $CH_2$ and $R^1$ is $CF_3$.

In a more preferred embodiment, the compound of formula (I') is selected from the following group:
N-(6-trifluoromethylbenzothiazole-2-yl)-2-(4-chlorophenyl)acetamide
N-(6-trifluoromethylbenzothiazole-2-yl)-2-(2-chlorophenyl)acetamide
N-(6-trifluoromethylbenzothiazole-2-yl)-2-(3-chlorophenyl)acetamide
N-(6-trifluoromethoxybenzothiazole-2-yl)-2-(3,4,5-trimethoxyphenyl)acetamide
N-(6-trifluoromethylbenzothiazole-2-yl)-2-(4-methoxyphenyl)acetamide
N-(6-trifluoromethylbenzothiazole-2-yl)-2-(3-methoxyphenyl)acetamide
N-(6-trifluoromethylbenzothiazole-2-yl)-2-(2-methoxyphenyl)acetamide
N-(6-trifluoromethylbenzothiazole-2-yl)-2-(3,4,5-trimethoxyphenyl)acetamide
N-(6-trifluoromethylbenzothiazole-2-yl)-2-phenylacetamide
N-(6-trifluoromethylbenzothiazole-2-yl)-2,2-diphenylacetamide
N-(benzothiazole-2-yl)-2-(3-chlorophenyl)acetamide
N-(6-methoxybenzothiazole-2-yl)-2-(3-chlorophenyl)acetamide
N-(6-trifluoromethoxybenzothiazole-2-yl)-2-(3-chlorophenyl)acetamide
N-(6-trifluoromethylbenzothiazole-2-yl)-N'-(3-chlorophenyl)urea
N-(6-trifluoromethoxybenzothiazole-2-yl)-2-(3,4-dichlorophenyl)acetamide
N-(6-trifluoromethylbenzothiazole-2-yl)-2-(2,5-dimethoxyphenyl)acetamide
N-(benzothiazole-2-yl)-2-benzyloxyacetamide
N-(benzothiazole-2-yl)-2-(2,2'-diphenylacetamide)acetamide
N-(6-trifluoromethylbenzothiazole-2-yl)-N'-(4-methoxyphenyl)urea
(E)-N-(6-(N,N-dimethylsulfamoyl)benzothiazole-2-yl)-3-(3,4,5-trimethoxyphenyl) acrylamide or its pharmaceutically acceptable salts, solvates or tautomers.

In an even more preferred embodiment, the compound of formula (I') is selected from the following group:
N-(6-trifluoromethylbenzothiazole-2-yl)-2-(4-chlorophenyl)acetamide
N-(6-trifluoromethylbenzothiazole-2-yl)-2-(2-chlorophenyl)acetamide
N-(6-trifluoromethylbenzothiazole-2-yl)-2-(3-chlorophenyl)acetamide
N-(6-trifluoromethoxybenzothiazole-2-yl)-2-(3,4,5-trimethoxyphenyl)acetamide
N-(6-trifluoromethylbenzothiazole-2-yl)-2-(4-methoxyphenyl)acetamide
N-(6-trifluoromethylbenzothiazole-2-yl)-2-(3-methoxyphenyl)acetamide
N-(6-trifluoromethylbenzothiazole-2-yl)-2-(2-methoxyphenyl)acetamide
N-(6-trifluoromethylbenzothiazole-2-yl)-2-(3,4,5-trimethoxyphenyl)acetamide
N-(6-trifluoromethylbenzothiazole-2-yl)-2-phenylacetamide
N-(6-trifluoromethylbenzothiazole-2-yl)-2,2-diphenylacetamide
N-(benzothiazole-2-yl)-2-(3-chlorophenyl)acetamide
N-(6-methoxybenzothiazole-2-yl)-2-(3-chlorophenyl)acetamide
N-(6-trifluoromethoxybenzothiazole-2-yl)-2-(3-chlorophenyl)acetamide
N-(6-trifluoromethylbenzothiazole-2-yl)-N'-(3-chlorophenyl)urea
N-(6-trifluoromethoxybenzothiazole-2-yl)-2-(3,4-dichlorophenyl)acetamide
N-(6-trifluoromethylbenzothiazole-2-yl)-2-(2,5-dimethoxyphenyl)acetamide or pharmaceutically acceptable salts, solvates or tautomers.

In a still more preferred embodiment, the compound of formula (I') is selected from the following group:
N-(6-trifluoromethylbenzothiazole-2-yl)-2-(4-chlorophenyl)acetamide
N-(6-trifluoromethylbenzothiazole-2-yl)-2-(4-methoxyphenyl)acetamide
N-(6-trifluoromethylbenzothiazole-2-yl)-2-(3-chlorophenyl)acetamide
N-(6-trifluoromethylbenzothiazole-2-yl)-2-(3-methoxyphenyl)acetamide
N-(6-trifluoromethylbenzothiazole-2-yl)-2-(2-methoxyphenyl)acetamide
N-(6-trifluoromethylbenzothiazole-2-yl)-2-(3,4,5-trimethoxyphenyl)acetamide
N-(6-trifluoromethylbenzothiazole-2-yl)-2-phenylacetamide or pharmaceutically acceptable salts, solvates or tautomers.

However, it should be noted that non-pharmaceutically acceptable salts also fall within the scope of the invention, since they may be useful for preparing pharmaceutically acceptable salts.

The compounds of the present invention are capable of crossing the blood-brain barrier, as shown in the examples below. This represents an additional advantage of the compounds when used in therapeutic treatments related to the central nervous system, such as the aforementioned neurodegenerative, neurological, psychiatric, inflammatory and autoimmune diseases.

Thus, the invention further relates to a compound of formula (I') for use as a drug.

An additional aspect of the present invention relates to a pharmaceutical composition comprising the compounds of formula (I') as defined above and at least one excipient, adjuvant and/or pharmaceutically acceptable vehicles.

The pharmaceutical compositions can be administered by any suitable administration route, for example: oral, parenteral (subcutaneous, intraperitoneal, intravenous, intramuscular, etc.), rectal, etc.

In a particular embodiment, said pharmaceutical compositions may be in a pharmaceutical form of oral administration, either solid or liquid. Illustrative examples of pharmaceutical forms of oral administration include tablets, capsules, granules, solutions, suspensions, etc., and may contain conventional excipients such as binders, dilutes, disintegrating agents, lubricants, humectants, etc., and may be prepared by conventional methods. The pharmaceutical compositions may also be adapted for parenteral administration, in the form of, for example, solutions, suspensions or lyophilised, sterile products in the suitable dosage form; in this case, said pharmaceutical compositions will include suitable excipients, such as buffers, surfactants, etc. In any case, the excipients are chosen according to the pharmaceutical form of administration selected. A review of the different pharmaceutical forms of drug administration and their preparation can be found in the book "Treatise on Galenic Pharmacy" by C. Faulí i Trillo, 10th Edition, 1993, Luzán 5, S. A. de Ediciones, or any book of similar characteristics in each country.

In a particular embodiment, for its administration in the treatment and/or prevention of diseases wherein CK-1 enzyme is relevant, the compounds of formula (I), their pharmaceutically acceptable salts and/or solvates will be formulated in an appropriate pharmaceutical composition, in the therapeutically effective quantity, together with one or more pharmaceutically acceptable excipients, adjuvants and/or carriers.

The term "treatment or prevention" as used herein, unless otherwise indicated, relates to reversing, alleviating and inhibiting the progress of, or preventing the disorder or condition to which it applies in such terms, one or more symptoms of such disorder or condition.

The term "excipients, adjuvants and/or carriers" relates to molecular entities or substances through which the active ingredient is administered. Such pharmaceutical excipients, adjuvants or carriers can be sterile liquids, such as water and oils, including those of petroleum, animal, vegetable or synthetic origin, such as peanut oil, soybean oil, mineral oil, sesame oil and similar oils, excipients, disintegrating agents, humectants or dilutes. Suitable pharmaceutical excipients and carriers are described in "Remington's Pharmaceutical Sciences" by E. W. Martin.

For its application in therapy, the compound of formula (I) will preferably be in a pharmaceutically acceptable or substantially pure form, that is, the compound of formula (I) has a pharmaceutically acceptable level of purity excluding pharmaceutically acceptable excipients and not including material considered toxic at normal dosage levels. The purity levels for a compound of formula (I) are preferably above 50%, more preferably above 70%, more preferably above 90%. In a preferred embodiment, they are above 95%.

In general, the therapeutically effective amount of the compound of formula (I) to be administered will depend, among other factors, on the individual who is to be treated, the severity of the disease suffered by the individual, the selected form of administration, etc. For this reason, the doses mentioned in this invention must be considered solely as guides for the skilled person, who must adjust the doses according to the aforementioned variables. However, a compound of formula (I) may be administered one or more times a day, for example 1, 2, 3 or 4 times a day, in a typical total daily quantity comprised between 0.1 and 1,000 mg/kg body weight/day, preferably 10 mg/kg body mass/day.

The compounds described in the present invention, their pharmaceutically acceptable tautomers, salts and solvates and pharmaceutical compositions containing them may be used together with other additional drugs to provide a combined therapy. Said additional drugs may form part of the same pharmaceutical composition or, alternatively, may be provided as a separate composition for simultaneous administration or not with the pharmaceutical composition comprising a compound of formula (I), an isomer, solvate or a pharmaceutically acceptable salt thereof.

Another aspect of the invention relates to a procedure (hereinafter, procedure 1) for preparing a compound of formula (I') as previously defined:

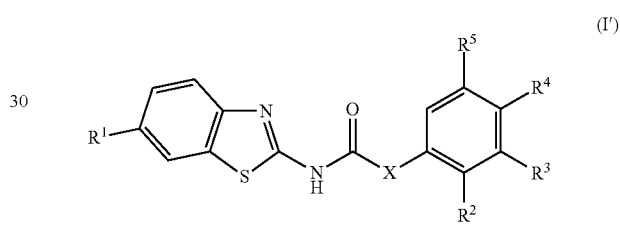

which comprises reacting a compound of formula (II):

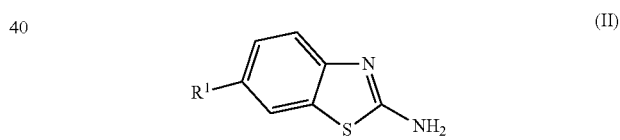

wherein $R^1$ is selected from among H, alquilo ($C_1$-$C_5$), halogen, $CF_3$, $OCF_3$, $OR^7$, $CO_2R^7$, $SO_2N(R^7)_2$ and $NO_2$, wherein $R^7$ is selected from among H and alkyl ($C_1$-$C_5$), with a compound of formula (III):

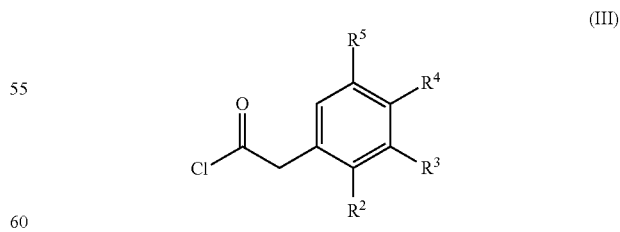

wherein $R^2$, $R^3$, $R^4$ and $R^5$ are independently selected from among H, halogen, O-alkyl ($C_1$-$C_5$),
in the presence or absence of a solvent, under microwave irradiation for a time interval comprised between 2 and 30 min, in a range of temperatures comprised between 100° C. and 200° C.

In a particular embodiment, when solvent is used it is tetrahydrofuran (THF).

In a preferred embodiment, the reaction time is set between 5 and 20 min.

In another preferred embodiment, the reaction temperature is set between 110° C. and 150° C.

The compound of formula (III) may be obtained by general procedures commonly known to a person skilled in the art based on the corresponding carboxylic acid, formula (IV) by treating it with thionyl chloride.

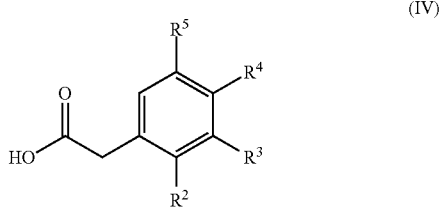

An alternative for preparing compounds of formula (I') consists of a process (hereinafter, procedure 2) which comprises reacting a compound of formula (II):

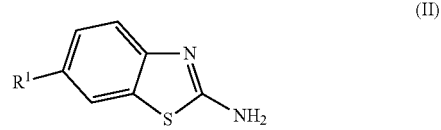

wherein $R^1$ is selected from among H, alkyl ($C_1$-$C_5$), halogen, $CF_3$, $OCF_3$, $OR^7$, $CO_2R^7$, $SO_2N(R^7)_2$ and $NO_2$, wherein $R^7$ is selected from among H and alkyl ($C_1$-$C_5$), with a compound of formula (V);

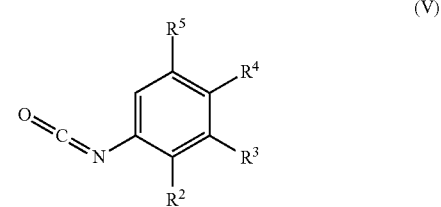

wherein $R^2$, $R^3$, $R^4$ and $R^5$ are independently selected from H, halogen, O-alkyl ($C_1$-$C_5$),
in the presence or absence of a solvent, under microwave irradiation for a time interval comprised between 0.5 and 5 hours, over a range of temperatures comprised between 100° C. and 200° C.

In a particular embodiment, when this solvent is used it is tetrahydrofuran (THF).

In a preferred embodiment, the reaction time is between 1 and 4 hours.

In another preferred embodiment, the reaction temperature is set between 110° C. and 150° C.

The compound of formula (V) may be obtained by general procedures commonly known to a person skilled in the art or may be purchased from a chemical supplier.

Another alternative for preparing compounds of formula (I') is a process (hereinafter, procedure 3) which comprises adding a compound of formula (II):

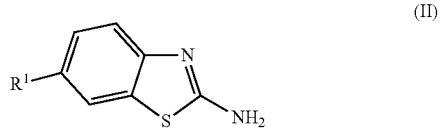

wherein $R^1$ is selected from among H, alkyl ($C_1$-$C_5$), halogen, $CF_3$, $OCF_3$, $OR^7$, $CO_2R^7$, $SO_2N(R^7)_2$ and $NO_2$, wherein $R^7$ is selected from among H and alkyl ($C_1$-$C_5$), on a solution comprising an aprotic organic solvent, a coupling agent, a base and a compound of formula (IV),

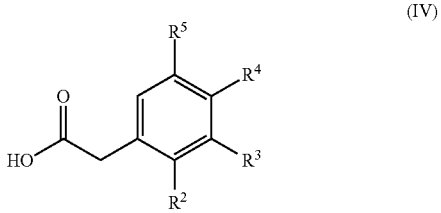

wherein $R^2$, $R^3$, $R^4$ and $R^5$ are independently selected from H, halogen, O-alkyl ($C_1$-$C_5$),
the reaction is completed within a time interval comprised between 0.5 and 24 hours and a temperature range is comprised between 0° C. and 60° C. is used.

In a particular embodiment, the solvent is selected from among tetrahydrofuran, dichloromethane and toluene.

In a particular embodiment, the coupling agent is benzotriazole-1-U-oxy-tris[pyrrolidine]phosphonium hexafluorophosphate (PyBOP).

In another particular embodiment, the base is selected from among triethylamine and diisopropylethylamine.

In a preferred embodiment, the reaction time is between 12 and 24 hours.

In another preferred embodiment, the temperature is set between 15° C. and 35° C.

In all the procedures (1-3), the compounds are isolated and purified by methods commonly known to a person skilled in the art.

EXAMPLES

Example 1

General Procedure for Synthesis of Compounds of the Invention

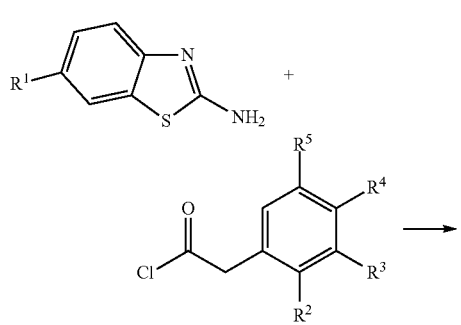

-continued

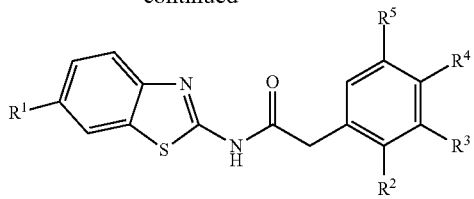

Acid Chloride Formation:

The corresponding acid (1 eq) and SOCl$_2$ (1.5 eq) is introduced in a flask having a coolant and under an inert atmosphere. The reaction mixture is heated at 80° C. for 6 hours. After this time has elapsed, the excess SOCl$_2$ evaporated under reduced pressure and the acid chloride obtained is used directly in the amide formation reaction.

Amide Formation:

The acid chloride (1 eq) formed on the corresponding 2-aminobenzothiazole (1 eq) is added introduced in a microwave vial. The vial is introduced in the microwave reactor and heated to the temperature for the time indicated in each case. Dichloromethane (50 mL) is added and extracted with a 0.1 M HCl (50 mL) solution. Next, the organic phase is washed with saturated NaHCO$_3$ solution (50 mL) and then with saturated NaCl (50 mL) solution. The organic phase is dried over anhydrous MgSO$_4$ and the solvent removed under reduced pressure. The residue obtained was purified by flash column chromatography using Isolera One equipment. In all cases a mixture of hexane and ethyl acetate was used as eluent. All the acid chlorides required for the synthesis of the amide derivatives were synthesised in situ except: 2-(4-chlorophenyl)acetyl chloride, 2-(2,5-dimethoxyphenyl)acetyl chloride and 2-phenylbutanoyl chloride, which were purchased directly from the company Sigma Aldrich.

N-(6-trifluoromethylbenzothiazole-2-yl)-2-(4-chlorophenyl)acetamide (1)

Reagents: 2-(4-chlorophenyl)acetyl chloride (216.7 mg, 1.1 mmol) and 2-amino-6-trifluoromethylbenzothiazole (250 mg, 1.14 mmol). Reaction conditions: 5 min under microwave irradiation at 150° C. Purification by flash column chromatography using hexane/ethyl acetate (3:1) to obtain a white solid. Yield: 404.1 mg, 95%. Mp: 135° C.-137° C. $^1$H NMR (300 MHz, DMSO-d$_6$) δ: 12.84 (s, 1H), 8.48 (s, 1H), 7.90 (d, J=8.5 Hz, 1H), 7.73 (d, J=8.4 Hz, 1 H), 7.49-7.27 (m, 4H), 3.87 (s, 2H). $^{13}$C NMR (75 MHz, DMSO-d$_6$) δ: 170.4, 161.1, 151.2, 134.0, 133.4, 132.0, 131.3, 128.1, 124.5 (d, J=272.0 Hz), 123.7 (d, J=31.8 Hz), 122.9 (d, J=3.9 Hz), 120.9, 119.9 (d, J=4.3 Hz) 41.0. HPLC purity: >99%. ESI-MS (m/z): 371 [M+H]$^+$. Elemental analysis (C$_{16}$H$_{10}$ClF$_3$N$_2$OS): Theoretical % C, 51.83, % H, 2.72, % N, 7.56, % S 8.64; Found % C, 52.00, % H, 2.71, % N, 7.55, % S 8.49.

N-(6-trifluoromethylbenzothiazole-2-yl)-2-(4-methoxyphenyl)acetamide (3)

Reagents: 2-(4-methoxyphenyl)acetyl chloride (21 1.7 mg, 1.2 mmol), 2-amino-6-trifluoromethylbenzothiazole (250 mg, 1.2 mmol) and THF (1 mL). Reaction conditions: 10 min under microwave irradiation at 110° C. Purification by flash column chromatography using hexane/ethyl acetate (3:1) to obtain a yellow solid. Yield: 184.8 mg, 44%. Mp: 133° C.-134° C. $^1$H NMR (300 MHz, DMSO-d$_6$) δ: 12.79 (s, 1H), 8.47 (s, 1H), 7.90 (d, J=8.5 Hz, 1H), 7.73 (d, J=8.5 Hz, 1H), 7.26 (d, J=8.6 Hz, 2H), 6.89 (d, J=8.7 Hz, 2H), 3.77 (s, 2H), 3.72 (s, 3H). $^{13}$C NMR (75 MHz, DMSO-d$_6$) δ: 171.0, 161.1, 158.3, 151.3, 132.0, 130.4, 126.3, 124.5 (d, J=272.2 Hz), 123.7 (d, J=31.9 Hz), 122.9 (d, J=3.7 Hz), 120.9, 119.8 (d, J=4.3 Hz), 113.9, 55.0, 40.9. HPLC purity: >99%. MS (ES) m/z: 367 [M+H]$^+$. Elemental analysis (C$_{17}$H$_{13}$F$_3$N$_2$O$_2$S): Theoretical % C, 55.73, % H, 3.58, % N, 7.65, % S 8.75; Found % C, 55.48, % H, 3.31, % N, 7.44, % S 8.97.

N-(6-trifluoromethylbenzothiazole-2-yl)-2-(3-chlorophenyl)acetamide (4)

Reagents: 2-(3-chlorophenyl)acetyl chloride (432.8 mg, 2.3 mmol), 2-amino-6-trifluoromethylbenzothiazole (500 mg, 2.3 mmol) and THF (1 mL). Reaction conditions: 10 min under microwave irradiation at 110° C. Purification by flash column chromatography using hexane/ethyl acetate (3:1) to obtain a white solid. Yield: 340 mg, 40%. Mp: 183° C.-185° C. $^1$H NMR (300 MHz, DMSO-d$_6$) δ: 12.85 (s, 1H), 8.48 (s, 1H), 7.91 (d, J=8.5 Hz, 1H), 7.73 (d, J=8.2 Hz, 1H), 7.44 (s, 1H), 7.35 (t, J=8.1 Hz, 3H), 3.90 (s, 2H). $^{13}$C NMR (75 MHz, DMSO-d$_6$) δ: 170.2, 161.1, 151.3, 136.8, 132.9, 132.0, 130.2, 129.4, 128.3, 127.0, 123.8 (d, J=31.8 Hz), 122.9 (d, J=3.2 Hz), 121.0, 119.9 (d, J=4.5 Hz), 41.2. HPLC purity: >99%. MS (ES) m/z: 371 [M+H]$^+$. Elemental Analysis (C$_{16}$H$_{10}$ClF$_3$N$_2$OS): Theoretical % C, 51.83, % H, 2.72, % N, 7.56, % S 8.75; found % C, 51.72, % H, 2.83, % N, 7.27, % S 8.56.

N-(6-trifluoromethylbenzothiazole-2-yl)-2-(3-methoxyphenyl)acetamide (6)

Reagents: 2-(3-methoxyphenyl)acetyl chloride (211.7 mg, 1.2 mmol), 2-amino-6-trifluoromethylbenzothiazole (250 mg, 1.2 mmol) and THF (1 mL). Reaction conditions: 15 min under microwave irradiation at 110° C. Purification by flash column chromatography using hexane/ethyl acetate (3:1) to obtain a white solid. Yield: 108.1 mg, 26%. Mp: 154° C.-156° C. $^1$H NMR (400 MHz, DMSO-d$_6$) δ: 12.83 (s, 1H), 8.48 (s, 1H), 7.90 (d, J=8.5 Hz, 1H), 7.73 (dd, J=8.5, 1.5 Hz, 1H), 7.25 (t, J=7.9 Hz, 1H), 6.92 (m, 2H), 6.84 (dd, J=7.9, 2.2 Hz, 1H), 3.82 (s, 2H), 3.74 (s, 2H). $^{13}$C NMR (101 MHz, DMSO-d$_6$) δ: 171.2, 161.8, 160.0, 152.0, 136.5, 132.7, 130.2, 125.2 (d, J=271.8 Hz), 124.4 (d, J=31.9 Hz), 123.6 (d, J=3.6 Hz), 122.2, 121.6, 120.6 (d, J=4.1 Hz), 115.9, 113.0, 55.7, 42.6. HPLC purity: 98%. MS (ES) m/z: 367 [M+H]$^+$. Elemental Analysis (C$_{17}$H$_{13}$F$_3$N$_2$O$_2$S): Theoretical % C, 55.73, % H, 3.58, % N, 7.65, % S 8.75; found % C, 55.80, % H, 3.41, % N, 7.66, % S 9.02N, 9.02% S.

N-(6-trifluoromethylbenzothiazole-2-yl)-2-(2-chlorophenyl)acetamide (7)

Reagents: 2-(2-chlorophenyl)acetyl chloride (216.6 mg, 1.2 mmol), 2-amino-6-trifluoromethylbenzothiazole (250 mg, 1.2 mmol). Reaction conditions: 5 min under microwave irradiation at 150° C. Purification by flash column chromatography using hexane/ethyl acetate (3:1) to obtain a white solid. Yield: 318.3 mg, 75%. Mp: 226° C.-228° C. $^1$H NMR (300 MHz, DMSO-d$_6$) δ: 12.92 (s, 1H), 8.49 (s, 1H), 7.91 (d, J=8.5 Hz, 1 H), 7.74 (dd, J=8.6, 1.9 Hz, 1H), 7.48-7.45 (m, 2H), 7.38-7.22 (m, 2H), 4.06 (s, 2H). $^{13}$C NMR (75 MHz, DMSO-d$_6$) δ: 169.7, 161.1, 151.3, 133.7, 132.6, 132.5, 132.0, 129.1, 127.3, 124.6 (d, J=271.9 Hz), 125.9, 124.3, 123.8 (d, J=31.8 Hz), 123.0 (d, J=3.5 Hz), 123.9, 123.0, 121.0, 119.9 (d, J=4.0 Hz), 120.0, 40.4. HPLC purity: >99%. MS (ES) m/z: 371 [M+H]⁺. Elemental analysis ($C_{16}H_{10}ClF_3N_2OS$): Theoretical % C, 51.83, % H, 2.72, % N, 15.37, % S 11.36; found % C, 51.68, % H, 2.54, % N, 7.50, % S 11.08.

N-(6-trifluoromethylbenzothiazole-2-yl)-2-(2-methoxyphenyl)acetamide (8)

Reagents: 2-(2-methoxyphenyl)acetyl chloride (211.6 mg, 1.2 mmol), 2-amino-6-trifluoromethylbenzothiazole (250 mg, 1.2 mmol). Reaction conditions: 5 min under microwave irradiation at 150° C. Purification by flash column chromatography using hexane/ethyl acetate (3:1) to obtain a white solid. Yield: 366.06 mg, 54%. Mp: 174° C.-175° C. ¹H NMR (300 MHz, DMSO-$d_6$) δ: 12.72 (s, 1H), 8.47 (s, 1H), 7.90 (d, J=8.5 Hz, 1H), 7.73 (d, J=8.5 Hz, 1 H), 7.48-7.09 (m, 2H), 6.99 (d, J=8.2 Hz, 1H), 6.92 (t, J=7.4 Hz, 1H), 3.84 (s, 2H), 3.74 (s, 3H). ¹³C NMR (75 MHz, DMSO-$d_6$) δ: 170.8, 161.2, 157.3, 151.4, 132.0, 131.2, 128.5, 124.6 (d, J=271.8 Hz), 123.6 (d, J=31.8 Hz), 122.9 (d, J=5.2 Hz), 122.8, 120.8, 120.2, 119.9 (d, J=4.2 Hz), 110.8, 55.5, 36.7. HPLC purity: 97%. MS (ES) m/z: 367 [M+H]⁺. Elemental analysis ($C_{17}H_{13}F_3N_2O_2S$): Theoretical % C, 55.73, % H, 3.58, % N, 7.65, % S 8.75; found % C, 56.02, % H, 3.61, % N, 7.37, % S 8.75.

N-(6-trifluoromethylbenzothiazole-2-yl)-2-(3,4-dichlorophenyl)acetamide (9)

Reagents: 2-(3,4-dichlorophenyl)acetyl chloride (256 mg, 1.2 mmol), 2-amino-6-trifluoromethylbenzothiazole (250 mg, 1.2 mmol) and THF (1 mL). Reaction conditions: 10 min under microwave irradiation at 110° C. Purification by flash column chromatography using hexane/ethyl acetate (1:1) to obtain a white solid. Yield: 405.18 mg, 65%. Mp: 158° C.-159° C. ¹H NMR (300 MHz, DMSO-$d_6$) δ: 12.85 (s, 1H), 8.49 (s, 1H), 7.91 (d, J=8.5 Hz, 1H), 7.73 (d, J=8.5 Hz, 1H), 7.64 (d, J=1.8 Hz, 1H), 7.61 (d, J=8.3 Hz, 1H), 7.34 (dd, J=8.3, 1.9 Hz, 1H), 3.92 (s, 2H). ¹³C NMR (75 MHz, DMSO-$d_6$) δ: 170.0, 161.0, 151.3, 135.4, 132.0, 131.7, 130.8, 130.4, 130.1, 129.7, 124.5 (d, J=272.0 Hz), 123.8 (d, J=31.8 Hz), 122.9 (d, J=3.4 Hz), 121.0, 119.9 (d, J=4.1 Hz), 40.5. HPLC purity: 97%. MS (ES) m/z: 406 [M+H]⁺. Elemental analysis ($C_{16}H_9F_3Cl_2N_2OS$): Theoretical % C, 47.42, % H, 2.24, % N, 14.07, % S 7.91; Found % C, 47.28, % H, 2.30, % N, 7.04, % S 7.38.

N-6-trifluoromethylbenzothiazole-2-yl)-2-(3,4,5-trimethoxyphenyl)acetamide (10)

Reagents: 2-(3,4,5-trimethoxyphenyl)acetyl chloride (280.1 mg, 1.2 mmol), 2-amino-6-trifluoromethylbenzothiazole (250 mg, 1.2 mmol) and THF (1 mL). Reaction conditions: 10 min under microwave irradiation at 110° C. Purification by flash column chromatography using hexane/ethyl acetate (1:1) to obtain a beige solid. Yield: 89.5 mg, 18%. Mp: 223° C.-224° C. ¹H NMR (300 MHz, DMSO-$d_6$) δ: 12.80 (s, 1H), 8.49 (s, 1H), 7.91 (d, J=8.2 Hz, 1H), 7.74 (d, J=8.9 Hz, 1H), 6.69 (s, 2H), 3.79 (s, 2H), 3.77 (s, 3H), 3.64 (s, 2H). ¹³C NMR (75 MHz, DMSO-$d_6$) δ: 171.0, 161.5, 153.1 (2C), 151.7, 136.9, 132.4, 130.2, 124.9 (d, J=272.0 Hz), 124.1 (d, J=31.8 Hz), 123.3 (d, J=3.5 Hz), 121.3, 120.3, 119.9 (d, J=4.2 Hz), 107.2, 60.3, 56.2 (2C), 42.5. HPLC purity: 98%. MS (ES) m/z: 427 [M+H]⁺. Elemental analysis ($C_{19}H_{17}F_3N_2O_4S$): Theoretical % C, 53.52, % H, 4.02, % N, 6.57, % S 7.52; found % C, 53.60, % H, 4.04, % N, 6.62, % S 7.71.

N-(6-trifluoromethoxybenzothiazole-2-yl)-2-(3,4,5-trimethoxyphenyl)acetamide (11)

Reagents: 2-(3,4,5-trimethoxyphenyl)acetyl chloride (261.1 mg, 1.1 mmol), 2-amino-6-trifluoromethoxybenzothiazole (250 mg, 1.1 mmol) and THF (1.5 mL). Reaction conditions: 10 min under microwave irradiation at 110° C. Purification by flash column chromatography using hexane/ethyl acetate (1:1) to obtain a brown solid. Yield: 89.3 mg, 19%. Mp: 224° C.-227° C. ¹H NMR (300 MHz, DMSO-$d_6$) δ: 12.66 (s, 1 H), 8.10 (d, J=1.2 Hz, 1 H), 7.81 (d, J=8.8 Hz, 1H), 7.41 (ddd, J=8.8, 2.4, 0.9 Hz, 1H), 6.67 (s, 2H), 3.76 (s, 8H), 3.62 (s, 3H). ¹³C NMR (75 MHz, DMSO-$d_6$) δ: 170.4, 159.5, 152.8 (2C), 147.5, 144.1, 136.5, 132.6, 129.9, 121.8, 120.2 (d, J=255.8 Hz), 118.5, 115.0, 106.8 (2C), 59.9, 55.8 (2C) 42.1. HPLC purity: >99%. MS (ES) m/z: 443 [M+H]⁺.

N-(6-trifluoromethylbenzothiazole-2-yl)-2-phenylacetamide (12)

Reagents: 2-phenylacetyl chloride (176.2 mg, 1.2 mmol), 2-amino-6-trifluoromethylbenzothiazole (250 mg, 1.2 mmol). Reaction conditions: 5 min under microwave irradiation at 150° C. Purification by flash column chromatography using hexane/ethyl acetate (1:1) to obtain a white-yellow solid. Yield: 234.3 mg, 61%. Mp: 211° C.-214° C. ¹H NMR (300 MHz, DMSO-$d_6$) δ: 12.46 (s, 1 H), 7.67-7.55 (m, 3H), 7.52 (d, J=2.1 Hz, 1H), 7.38-7.29 (m, 1H), 7.00 (dd, J=8.8, 2.2 Hz, 1H), 3.85 (s, 2H). ¹³C NMR (75 MHz, DMSO-$d_6$) δ: 171.1, 161.5, 151.6, 134.8, 132.4, 129.7 (2C), 128.8 (2C), 127.3, 125.8 (d, J=36.1 Hz), 124.9 (d, J=267.0 Hz), 123.3 (d, J=3.3 Hz), 121.3, 120.3 (d, J=3.8 Hz), 42.2. HPLC purity: >99%. MS (ES) m/z: 336 [M+H]⁺.

N-(6-trifluoromethylbenzothiazole-2-yl)-2-(3-(trifluoromethyl)phenyl)acetamide (13)

Reagents: 2-(3-(trifluoromethyl)phenyl)acetyl chloride (253.8 mg, 1.2 mmol), 2-amino-6-trifluoromethylbenzothiazole (250 mg, 1.2 mmol) and THF (0.5 mL). Reaction conditions: 20 min under microwave irradiation at 110° C. Purification by flash column chromatography using hexane/ethyl acetate (1:1) to obtain a white solid. Yield: 194.4 mg, 42%. Mp: 138-140° C. ¹H NMR (400 MHz, DMSO-$d_6$) δ: 12.87 (s, 1H), 8.48-8.43 (m, 1 H), 7.88 (d, J=8.5 Hz, 1H), 7.74-7.51 (m, 5H), 3.99 (s, 2H). ¹³C NMR (101 MHz, DMSO-$d_6$) δ: 170.9, 161.7, 151.9, 136.4, 134.5, 132.7, 130.1, 129.7 (d, J=31.5 Hz.), 126.9 (d, J=3.9 Hz), 125.2 (d, J=271.8 Hz), 124.9 (d, J=272.1 Hz), 124.4 (d, J=3.8 Hz), 124.4 (d, J=31.8 Hz), 123.6 (d, J=4.0 Hz), 121.7, 120.6 (d, J=4.4 Hz), 41.9. HPLC purity: 96%. MS (ES) m/z: 405 [M+H]⁺.

N-(6-trifluoromethylbenzothiazole-2-yl)-2,2-diphenylacetamide (15)

Reagents: 2,2-diphenylacetyl chloride (264.6 mg, 1.2 mmol), 2-amino-6-trifluoromethylbenzothiazole (250 mg, 1.2 mmol) and THF (0.5 mL). Reaction conditions: 10 min under microwave irradiation at 110° C. Purification by flash column chromatography using hexane/ethyl acetate (3:1) to obtain a white solid. Yield: 299.3 mg, 63%. Mp: 144° C.-146° C. ¹H NMR (300 MHz, DMSO-$d_6$) δ: 13.11 (s, 1H), 12.72 (s, 1H), 8.52 (s, 1H), 7.91 (d, J=8.5 Hz, 1H), 7.75 (d, J=8.6 Hz, 1 H), 7.44-7.15 (m, 10H), 5.43 (s, 1H). $^{13}$C NMR (75 MHz, DMSO-d$_6$). δ: 171.8, 161.4, 151.6, 139.0 (2C), 132.4, 129.0 (4C), 129.0 (4C), 127.7 (2C), 124.9 (d, J=272.0 Hz), 124.2 (d, J=31.7 Hz), 123.4 (d, J=3.6 Hz), 121.4, 120.3 (d, J=4.8 Hz), 56.6. HPLC purity: 97%. MS (ES) m/z: 413 [M+H]$^+$. Elemental analysis (C$_{22}$H$_{15}$F$_3$N$_2$OS): Theoretical % C, 64.07, % H, 3.67, % N, 6.79, % S 7.77; found % C, 65.33, % H, 4.08, % N, 6.11, % S 6.52.

N-(benzothiazole-2-yl)-2-(3-chlorophenyl)acetamide (20)

Reagents: 2-(3-chlorophenyl)acetyl chloride (629.5 mg, 3.3 mmol), 2-aminobenzothiazole (500 mg, 3.3 mmol) and THF (1 mL). Reaction conditions: 10 min under microwave irradiation at 110° C. Purification by flash column chromatography using hexane/ethyl acetate (3:1) to obtain a white solid. Yield: 205.3 mg, 20%. Mp: 155° C.-157° C. $^1$H NMR (300 MHz, DMSO-d$_6$) δ: 12.60 (s, 1H), 7.96 (d, J=7.2 Hz, 1H), 7.74 (d, J=8.1 Hz, 1H), 7.53-7.19 (m, 6H), 3.86 (s, 2H). $^{13}$C NMR (75 MHz, CDCl$_3$) δ: 168.9, 159.2, 147.7, 134.8, 134.7, 131.9, 130.1, 129.4, 127.9, 127.3, 126.5, 124.2, 121.7, 120.4, 42.6. HPLC purity: >99%. MS (ES) m/z: 304 [M+H]$^+$. Elemental analysis (C$_{15}$H$_{11}$ClN$_2$OS): Theoretical % C, 59.50, % H, 3.66, % N, 9.25, % S 10.59; found % C, 59.80, % H, 3.59, % N, 9.27, % S 10.31.

N-(6-methoxybenzothiazole-2-yl)-2-(3-chlorophenyl)acetamide (22)

Reagents: 2-(3-chlorophenyl)acetyl chloride (314.6 mg, 1.7 mmol), 2-amino-6-methoxybenzothiazole (300 mg, 1.7 mmol) and THF (1 mL). Reaction conditions: 15 min under microwave irradiation at 1100° C. Purification by flash column chromatography using hexane/ethyl acetate (3:1) to obtain a white solid. Yield: 418 mg, 76%. Mp: 173° C.-175° C. $^1$H NMR (300 MHz, DMSO-d$_6$) δ: 12.47 (s, 1H), 7.63 (d, 1H, J=8.9 Hz), 7.52 (d, 1H, J=2.5 Hz), 7.41 (m, 1H) 7.38-7.2 (m, 3H), 7.00 (dd, 1H, J=8.9 Hz, J=2.6 Hz), 3.82 (s, 2H), 3.77 (s, 3H). $^{13}$C NMR (75 MHz, DMSO-d$_6$) δ: 169.7, 156.4, 156.0, 142.7, 137.3, 133.1, 132.9, 130.5, 129.5, 128.4, 127.1, 121.4 115.2, 104.9, 55.8, 41.4. HPLC purity: >99%. MS (ES) m/z: 333 [M+H]$^+$. Elemental analysis (C$_{16}$H$_{13}$ClN$_2$O$_2$S): Theoretical % C, 57.74, % H, 3.94, % N, 8.42, % S 9.63; found % C, 57.46, % H, 3.90, % N, 8.27, % S 9.44.

N-(6-trifluoromethoxybenzothiazole-2-yl)-2-(3-chlorophenyl)acetamide (23)

Reagents: 2-(3-chlorophenyl)acetyl chloride (201.7 mg, 1.1 mmol), 2-amino-6-trifluoromethoxybenzothiazole (250 mg, 1.1 mmol). Reaction conditions: 5 min under microwave irradiation at 150° C. Purification by flash column chromatography using hexane/ethyl acetate (1:1) to obtain a white solid. Yield: 386.7 mg, 48%. Mp: 174° C.-176° C. $^1$H NMR (300 MHz, DMSO-d$_6$) δ: 12.74 (s, 1H), 8.11 (t, J=1.8 Hz, 1H), 7.82 (dd, J=8.8, 1.7 Hz, 1 H), 7.47-7.25 (m, 5H), 3.88 (s, 2H). $^{13}$C NMR (101 MHz, DMSO-d$_6$) δ: 170.7, 160.0, 148.2, 144.7, 137.5, 133.6, 133.3, 130.9, 130.1, 128.9, 127.6, 122.2, 120.9 (d, J=256.1 Hz), 119.6, 115.7, 41.8. HPLC purity: 98%. MS (ES) m/z: 387 [M+H]$^+$. Elemental Analysis (C$_{16}$H$_{10}$ClF$_3$N$_2$O$_2$S): Theoretical % C, 49.68, % H, 2.61, % N, 7.24, % S 8.29; found % C, 49.81, % H, 2.45, % N, 7.32, % S 7.99.

N-(6-trifluoromethoxybenzothiazole-2-yl)-2-(3,4-dichlorophenyl)acetamide (28)

Reagents: 2-(3,4-dichlorophenyl)acetyl chloride (238.5 mg, 1.1 mmol), 2-amino-6-trifluoromethoxybenzothiazole (250 mg, 1.1 mmol) and THF (0.3 mL). Reaction conditions: 10 min under microwave irradiation at 110° C. Purification by flash column chromatography using hexane/ethyl acetate (1:1) to obtain a white solid. Yield: 203.1 mg, 45%. Mp: 170° C.-172° C. $^1$H NMR (300 MHz, DMSO-d$_6$) δ: 7.97 (s, 1H), 7.76-7.64 (m, 1 H), 7.65-7.52 (m, 2H), 7.33 (dd, J=8.1, 1.7 Hz, 2H), 3.82 (s, 2H). $^{13}$C NMR (75 MHz, DMSO-d$_6$) δ: 171.4, 162.0, 148.1, 143.5, 136.7, 132.9, 131.5, 130.6, 130.3, 130.0, 129.3, 121.9, 120.2 (d, J=255.9 Hz), 118.5, 114.6, 41.7. HPLC purity: >99%. MS (ES) m/z: 422 [M+H]$^+$. Elemental analysis (C$_{16}$H$_9$Cl$_2$F$_3$N$_2$O$_2$S): Theoretical % C, 45.62, % H, 2.15, % N, 6.65, % S 7.62; found % C, 45.38, % H, 1.97, % N, 6.48, % S 7.47.

N-(6-trifluoromethylbenzothiazole-2-yl)-2-(2,5-dimethoxyphenyl)acetamide (29)

Reagents: 2-(2,5-dimethoxyphenyl)acetyl chloride (246 mg, 1.2 mmol), 2-amino-6-trifluoromethylbenzothiazole (250 mg, 1.2 mmol). Reaction conditions: 7 min under microwave irradiation at 150° C. Purification by flash column chromatography using hexane/ethyl acetate (3:1) to obtain a beige solid. Yield: 141.7 mg, 31%. Mp. 146° C.-147° C. $^1$H NMR (300 MHz, DMSO-d$_6$) δ: 8.26 (d, J=24.7 Hz, 1H), 7.63 (dd, J=32.9, 7.4 Hz, 2H), 6.82 (dd, J=30.0, 9.1 Hz, 3H), 3.68 (s, 8H). $^{13}$C NMR (75 MHz, DMSO-d$_6$) δ: 174.0, 165.95, 152.9, 152.6, 151.5, 132.5, 125.9, 121.9 (d, J=2.25 Hz), 121.6 (d, J=37.2 Hz), 119.2, 118.8 (d, J=3.6 Hz), 117.4, 111.7 (2C), 56.0, 55.3, 38.4. HPLC purity: >99%. MS (ES) m/z: 397 [M+H]$^+$.

N-(6-methylbenzothiazole-2-yl)-2-(2-methoxyphenyl)acetamide (30)

Reagents: 2-(2-methoxyphenyl)acetyl chloride (280.8 mg, 1.5 mmol), 2-amino-6-methylbenzothiazole (250 mg, mmol). Reaction conditions: 5 min under microwave irradiation at 150° C. Purification by flash column chromatography using hexane/ethyl acetate (1:1) to obtain an orange-brown solid. Yield: 93.45 mg, 20%. Mp: 165° C.-167° C. $^1$H NMR (300 MHz, DMSO-d$_6$) δ: 12.38 (s, 1 H), 7.73 (s, 1 H), 7.61 (d, J=8.2 Hz, 1 H), 7.32-7.16 (m, 1 H), 6.98 (d, J=7.7 Hz, 1H), 6.91 (td, J=7.4, 10.0 Hz, 1 H), 3.79 (s, 1H), 3.74 (s, 1 H), 2.39 (s, 1H). $^{13}$C NMR (75 MHz, DMSO-d$_6$) δ: 170.1, 157.2, 157.1, 146.5, 132.8, 131.5, 131.1, 128.4, 127.3, 123.0 121.0, 120.2, 120.1, 110.8, 55.4, 36.6, 20.9. HPLC purity: >99%. MS (ES) m/z: 312 [M+H]$^+$.

N-(6-methoxybenzothiazole-2-yl)-2-(3,4-dichlorophenyl)acetamide (53)

Reagents: 2-(3,4-dichlorophenyl)acetyl chloride (310 mg, 10.4 mmol), 2-Amino-6-methoxybenzothiazole (250 mg, 1.4 mmol) and THF (0.4 mL). Reaction conditions: 10 min under microwave irradiation at January 10° C. Purification by flash column chromatography using hexane/ethyl acetate (1:1) to obtain a beige solid. Yield: 100 mg, 20%. Mp: 198° C.-199° C. $^1$H NM R (300 MHz, DMSO-d$_6$) δ: 12.47 (s, 1H), 7.64-7.58 (m, 3H), 7.55 (d, J=2.7 Hz, 1H), 7.32 (d, J=8.4 Hz, 1H), 7.01 (dd, J=8.8, 2.7 Hz, 1H), 3.85 (s, 2H), 3.78 (s, 3H). $^{13}$C NMR (75 MHz, DMSO-d$_6$) δ: 169.8, 156.9, 156.4, 143.3, 136.5, 133.4, 132.3, 131 0.5, 131 0.1, 130.7, 130.3, 121.9 115.7, 105.4, 56.3, 41.2. HPLC purity: >99%. MS (ES) m/z: 368 [M+H]$^+$. Elemental analysis ($C_{16}H_{12}Cl_2N_2O_2S$): Theoretical % C, 52.33, % H, 3.29, % N, 7.63,% S 8.73. found % C, 52.05, % H, 3.09, % N, 7.38, % S 8.53.

Example 2

General Procedure for Synthesis of Compounds 24 and 46

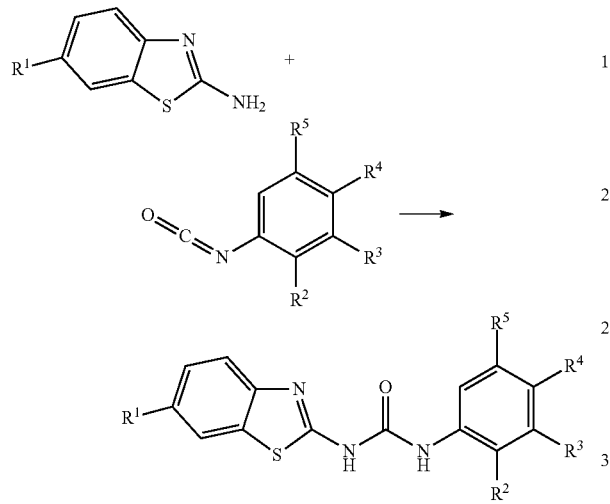

General Methodology: In a microwave vial benzothiazole derivative and the corresponding isocyanate is added in each case. Next, THF is added as solvent. The vial is introduced into the microwave reactor and heated to the temperature for the time indicated in each case. After the reaction time, ethyl acetate (50 mL) and water (50 mL) is added. The organic phase is dried over anhydrous $MgSO_4$ and the solvent is removed under reduced pressure. The obtained residue was purified by flash column chromatography using Isolera One equipment, in all cases a mixture of hexane and ethyl acetate as eluent was used.

N-(6-trifluoromethylbenzothiazole-2-yl)-N'-(3-chlorophenyl)urea (24)

Reagents: 1-isocianato-3-chlorobenzene (175.8 mg, 1.2 mmol), 2-amino-6-trifluoromethylbenzothiazole (250 mg, 1.2 mmol) and THF (0.4 mL). Reaction conditions: 3 hours and 30 min under microwave irradiation at 110° C. Purification by flash column chromatography using hexane/ethyl acetate (3:1) to obtain a white solid. Yield: 43.2 mg, 10%. Mp: 222° C.-223° C. $^1$H NMR (500 MHz, DMSO-$d_6$) δ: 11.16 (s, 1H), 9.38 (s, 1H), 8.41 (s, 1H), 7.73 (s, 1H), 7.69 (dd, J=8.5, 1.9 Hz, 1H), 7.38 (s, 1H), 7.35 (t, J=7.9 Hz, 2H), 7.11 (d, J=8.5 Hz, 1H). $^{13}$C NMR (126 MHz, DMSO-$d_6$) δ: 162.6, 152.0, 140.3, 133.7, 131.0, 125.0 (q, J=271.7 Hz), 123.6 (d, J=31.8 Hz), 123.5, 123.4 (d, J=2.5 Hz), 120.1 (d, J=4.3 Hz), 118.8, 117.9. HPLC purity: >99%. MS (ES) m/z: 372 [M+H]$^+$.

N-(6-trifluoromethylbenzothiazole-2-yl)-N'-(4-methoxyphenyl)urea (46)

Reagents: 1-isocianato-4-methoxybenzene (170.9 mg, 1.2 mmol), 2-amino-6-trifluoromethylbenzothiazole (250 mg, 1.2 mmol) and 0.4 mL of THF. Reaction conditions: 1 hour under microwave irradiation at 110° C. Purification by flash column chromatography using hexane/ethyl acetate (3:1) to obtain a white solid. Yield: 208.7 mg, 50%. Mp: 194° C.-196° C. $^1$H NMR (300 MHz, DMSO-$d_6$) δ: 10.97 (s, 1H), 8.99 (s, 1H), 8.39 (s, 1H), 7.79 (d, J=8.4 Hz, 1H), 7.72-7.62 (m, 1H), 7.41 (d, J=8.9 Hz, 2H), 6.91 (d, J=9.0 Hz, 2H), 3.72 (s, 3H). $^{13}$C NMR (75 MHz, DMSO-$d_6$) δ: 162.6, 160.8, 155.4, 151.8, 132.3, 131.1, 125.3 (d, J=39.6 Hz), 124.8 (d, J=242.6 Hz), 122.8 (d, J=2.7 Hz), 120.9 (2C), 119.5 (d, J=4.2 Hz), 119.5, 114.1 (2C), 55.2. HPLC purity: >99%. MS (ES) m/z: 368 [M+H]$^+$. Elemental analysis ($C_{16}H_{12}F_3N_3O_2S$): Theoretical % C, 52.31, % H, 3.29, % N, 11.44. found % C, 50.27, % H, 4.08, % N 11.54.

Example 3

General Procedure for Synthesis of Compounds 35, 37 and 38

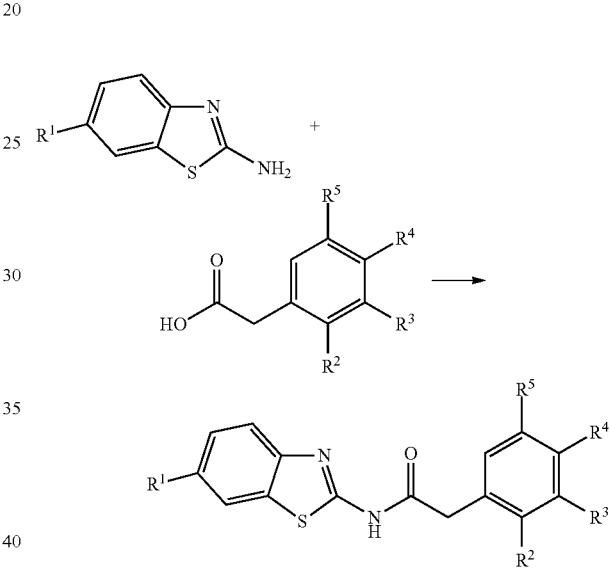

General Methodology: A solution of the corresponding carboxylic acid (1.2 eq) in dichloromethane (10 mL) is added in a round-bottomed flask. Next, the coupling agent (1.2 eq) and triethylamine (2 eq) is added. The reaction mixture is stirred for 1 hour at room temperature. After this time period has elapsed, the 2-aminobenzothiazole derivative (1 eq) is added and stirred at room temperature for the time indicated in each case. The solvent is removed under reduced pressure and the reaction crude is purified by the method indicated in each case.

N-(benzothiazole-2-yl)-2-benzyloxyacetamide (35)

It is obtained according to the general method described above. Reagents: 2-(benzyloxy)acetic acid (200 mg, 1.2 mmol), PyBOP (592 mg, 1.2 mmol), 2-aminobenzothiazole (147 mg, 1 mmol), TEA (0.26 mL, 1.9 mmol). Reaction conditions: stirring at room temperature for 12 hours. Purification: suspended solid filtration and washed with $CH_2Cl_2$ to obtain a white solid. Yield: 215 mg, 76%. Mp: 75.6° C. $^1$H NMR (300 MHz, CDCl$_3$) δ: 7.71-7.66 (m, 2H), 7.36-7.15 (m, 4H), 4.56 (s, 2H), 4.12 (s, 2H). $^{13}$C NMR (75 MHz, CDCl$_3$) δ: 167.4, 156.2, 146.7, 134.7, 130.6, 127.7, 127.5, 126.9, 124.9, 122.7, 120.4, 119.8, 72.7, 67.1. HPLC purity: >95%. MS (m/z): 299 (M+H)$^+$. Elemental analysis

N-(benzothiazole-2-yl)-2-(2,2-diphenylacetamide)acetamide (37)

It is obtained according to the general method described above. Reagents: 2-(2,2'-diphenylacetamide)acetic acid (150 mg, 0.6 mmol) which was previously obtained by reduction of 2-(2,2'-diphenylacetamide)benzyl acetate; PyBOP (288 mg, 0.6 mmol), 2-aminobenzothiazole (72 mg, 0.5 mmol), TEA (0.2 mL, 1.1 mmol). Reaction conditions: stirring at room temperature for 24 hours. Purification: flash column chromatography using Isolera One equipment, using hexane/ethyl acetate as eluent (6:1) to obtain a white solid. Yield: 18 mg, 10%. Mp. 208.2° C.-209.0° C. $^1$H NMR (300 MHz, CDCl$_3$) δ: 7.87 (d, J=7.4 Hz, 1H), 7.76 (d, J=8.6 Hz, 1H), 7.50-7.30 (m, 12H), 5.32 (s, 1H), 4.19 (d, J=5.6 Hz, 2H). $^{13}$C NMR (75 MHz, CDCl$_3$) δ: 170.8, 158.4, 148.5, 147.5, 137.9, 132.6, 129.5, 129.3, 128.4, 126.8, 124.6, 121.9, 121.2, 49.4, 40.1. HPLC purity: 98%. MS (m/z): 402 (M+H)$^+$. Elemental analysis (C$_{23}$H$_{19}$N$_3$O$_2$S): Theoretical % C, 68.81, % H, 4.77, % N, 10.47, % S 7.99; Found % C, 68.53, % H, 4.48, % N, 10.71, % S 7.86.

N-(benzothiazole-2-yl)-2-(2-phenylacetamide)acetamide (38)

EDC (296 mg, 1.6 mmol) along with DMAP (58 mg, 0.5 mmol) was added to a solution of 2-(2-phenylacetamide)acetic acid (305 mg, 1.6 mmol) in dichloromethane (10 mL) and stirred for 1 hour. Next, 2-aminobenzothiazole (200 mg, 1.3 mmol) was added and stirred at room temperature for 12 hours. Lastly, the solvent was removed by vacuum filtration. The residue obtained was purified by washing with CH$_2$Cl$_2$ to obtain a white solid. Yield: 327 mg, 78%. Mp: 247.2° C.-249.9° C. $^1$H NMR (300 MHz, CDCl$_3$) δ: 8.56 (t, J=5.7 Hz, 1 H), 7.96 (d, J=8.0 Hz, 1 H), 7.72 (d, J=8.1 Hz, 1 H), 7.41 (t, J=8.4 Hz, 1 H), 7.30-7.19 (m, 5H), 3.51 (s, 2H), 4.05 (d, J=5.6 Hz, 2H). $^{13}$C NMR (75 MHz, CDCl$_3$) δ: 171.5, 169.8, 158.9, 158.4, 149.1, 136.7, 129.8, 128.8, 127.1, 126.7, 124.2, 122.3, 42.9, 42.6. HPLC purity: >99%. MS (m/z): 326 (M+H)$^+$. Elemental analysis (C$_{17}$H$_{15}$N$_3$O$_2$S): Theoretical % C, 62.75, % H, 4.65, % N, 12.91, % S 9.85; Found % C, 62.47, % H, 4.58, % N, 12.67, % S 9.57.

Example 2

Measurement of the Inhibition of CK-1 in the Compounds of the Invention

Enzyme inhibition assays were performed using the Luminometer Kinase-GLO® method. Recombinant human enzyme CK-1δ was purchased from Millipore *Iberica* SAU and recombinant human enzyme CK-1ε was purchased from Invitrogen. The phosphorylation substration chosen was casein. The Luminescent Kinase Kit (catalogue no. V6711) was obtained from Promega. ATP and other reagents were purchased from Sigma-Aldrich (St. Louis, Mo.).

The assays were conducted in buffer using 96-well plates. In a typical assay: 10 μL of the test compound (dissolved in dimethylsulfoxide at a concentration of 1 mM and, in turn, dissolved in buffer to the required concentration for the experiment) and 10 μL (16 ng) of the CK-1δ enzyme or 10 μL (50 ng) of the CK-1ε enzyme row were added to each well followed by 20 μL of buffer containing 0.1% casein as substrate and 4 μM of ATP. The assay buffer contained: 50 mM HEPES, pH 7.5; 0.01% Brij-35; 10 mM MgCl$_2$; 1 mM EGTA and 0.01% NaN3. The final concentration of DMSO in the experiment did not exceed 1%. After incubating for 60 minutes at 30° C., the enzymatic reaction was stopped using 40 μL of Kinase-GLO® reagent. Luminescence was measured after ten minutes using a FLUOstar Optima (BMG Labtechnologies GmbH, Offenburg, Germany) multimode reader. The activity was proportional to the difference between the total and consumed ATP. Inhibition activities were calculated in accordance with the maximum activity measured in the absence of inhibitor. IC$_{50}$ is defined as the concentration of each compound that reduces enzyme activity by 50% with respect to that obtained without inhibitor.

TABLE 1

Inhibitory Concentration 50 (IC$_{50}$) of the compounds of the invention.

| No. | R$^1$ | X | R$^2$ | R$^3$ | R$^4$ | R$^5$ | CK-1δ μM | CK-1ε μM |
|---|---|---|---|---|---|---|---|---|
| 1 | CF$_3$ | CH$_2$ | H | H | Cl | H | 0.065 | 0.55 |
| 2 | Cl | CH$_2$ | H | H | OMe | H | 0.070 | 0.50 |
| 3 | CF$_3$ | CH$_2$ | H | H | OMe | H | 0.033 | 0.70 |
| 4 | CF$_3$ | CH$_2$ | H | Cl | H | H | 0.023 | 0.84 |
| 5 | Me | CH$_2$ | H | Cl | H | H | 0.083 | 0.88 |
| 6 | CF$_3$ | CH$_2$ | H | OMe | H | H | 0.042 | 0.69 |
| 7 | CF$_3$ | CH$_2$ | Cl | H | H | H | 0.068 | 7.73 |
| 8 | CF$_3$ | CH$_2$ | OMe | H | H | H | 0.010 | 0.80 |
| 9 | CF$_3$ | CH$_2$ | H | Cl | Cl | H | 0.056 | 0.87 |
| 10 | CF$_3$ | CH$_2$ | H | OMe | OMe | OMe | 0.015 | 0.37 |
| 11 | OCF$_3$ | CH$_2$ | H | OMe | OMe | OMe | 0.079 | 0.94 |
| 12 | CF$_3$ | CH$_2$ | H | H | H | H | 0.047 | 0.76 |

TABLE 1-continued

Inhibitory Concentration 50 (IC$_{50}$) of the compounds of the invention.

| No. | R$^1$ | X | R$^2$ | R$^3$ | R$^4$ | R$^5$ | CK-1δ μM | CK-1ε μM |
|---|---|---|---|---|---|---|---|---|
| 13 | CF$_3$ | CH$_2$ | H | CF$_3$ | H | H | 0.087 | 0.72 |
| 14 | H | CH$_2$ | H | H | H | H | 0.33 | 2.31 |
| 15 | CF$_3$ | CHPh | H | H | H | H | 0.26 | 2.75 |
| 16 | OMe | CHPh | H | H | H | H | 0.84 | 5.07 |
| 17 | NO$_2$ | CH$_2$CH$_2$ | H | H | H | H | 0.57 | 9.40 |
| 18 | H | CH$_2$ | H | H | F | H | 0.53 | 3.08 |
| 19 | OMe | CH$_2$ | H | H | OMe | H | 0.57 | 2.41 |
| 20 | H | CH$_2$ | H | Cl | H | H | 0.85 | 2.86 |
| 21 | OMe | CH$_2$ | H | H | Cl | H | 0.75 | 8.75 |
| 22 | OMe | CH$_2$ | H | Cl | H | H | 0.53 | 3.73 |
| 23 | OCF$_3$ | CH$_2$ | H | Cl | H | H | 0.54 | 1.02 |
| 24 | CF$_3$ | NH | H | Cl | H | H | 0.74 | 10.95 |
| 25 | OMe | CH$_2$ | H | OMe | H | H | 0.42 | 2.43 |
| 26 | OEt | CH$_2$ | H | OMe | H | H | 0.99 | 8.97 |
| 27 | OCF$_3$ | CH$_2$ | OMe | H | H | H | 0.62 | 7.39 |
| 28 | OCF$_3$ | CH$_2$ | H | Cl | Cl | H | 0.59 | 0.93 |
| 29 | CF$_3$ | CH$_2$ | OMe | H | H | OMe | 0.19 | 3.14 |
| 30 | Me | CH$_2$ | OMe | H | H | H | 0.29 | 4.93 |
| 31 | Cl | CH$_2$ | OMe | H | H | H | 0.32 | 1.15 |
| 32 | Br | CH$_2$ | OMe | H | H | H | 0.26 | 1.03 |
| 33 | H | CHPh | H | H | H | H | 1.96 | 7.31 |
| 34 | H | CH$_2$CHPh | H | H | H | H | 2.50 | 9.73 |
| 35 | H | CH$_2$OCH$_2$ | H | H | H | H | 4.37 | 48% @ 10 μM |
| 36 | H | CH$_2$NHCO | H | H | H | H | 7.29 | 48% a 10 μM |
| 37 | H | CH$_2$NHCOCHPh | H | H | H | H | 1.93 | 13 |
| 38 | H | CH$_2$NHCOCH$_2$ | H | H | H | H | 6.33 | 37% @ 10 μM |
| 39 | OEt | CHPh | H | H | H | H | 2.82 | 7.86 |
| 40 | CO$_2$Et | CHPh | H | H | H | H | 6.68 | 1.60 |
| 41 | SO$_2$NH$_2$ | CHPh | H | H | H | H | 10% @ 10 μM | 10% @ 10 μM |
| 42 | SO$_2$NHEt | CHPh | H | H | H | H | 10% @ 10 μM | 10% @ 10 μM |
| 43 | SO$_2$NHBu | CHPh | H | H | H | H | 10% @ 10 μM | 10% @ 10 μM |
| 44 | SO$_2$NEt$_2$ | CHPh | H | H | H | H | 9.83 | 3.47 |
| 45 | OEt | CH$_2$ | H | H | OMe | H | 1.09 | 9.49 |
| 46 | CF$_3$ | NH | H | H | OMe | H | 5.50 | 29% @ 10 μM |
| 47 | H | CH$_2$CH$_2$ | H | Cl | H | H | 3.58 | 31% @ 10 μM |
| 48 | OEt | CH$_2$ | H | Cl | H | H | 1.21 | 9.75 |
| 49 | OMe | CH$_2$ | Cl | H | H | H | 9.71 | 30% @ 10 μM |
| 50 | OEt | CH$_2$ | Cl | H | H | H | 17.43 | 20% @ 10 μM |
| 51 | OMe | CH$_2$ | OMe | H | H | H | 2.22 | 33% @ 10 μM |
| 52 | OEt | CH$_2$ | OMe | H | H | H | 5.76 | 46% @ 10 μM |

TABLE 1-continued

Inhibitory Concentration 50 ($IC_{50}$) of the compounds of the invention.

| No. | $R^1$ | X | $R^2$ | $R^3$ | $R^4$ | $R^5$ | CK-1δ μM | CK-1ε μM |
|---|---|---|---|---|---|---|---|---|
| 53 | OMe | $CH_2$ | H | Cl | Cl | H | 1.24 | 16.49 |
| 54 | OEt | $CH_2$ | H | Cl | Cl | H | 3.43 | 14.20 |
| 55 | OMe | $CH_2$ | H | OMe | OMe | OMe | 6.65 | 17.73 |
| 56 | OEt | $CH_2$ | H | OMe | OMe | OMe | 1.43 | 9.83 |
| 57 | $SO_2NMe_2$ | CHCH | H | OMe | OMe | OMe | 10% @ 10 μM | 10% @ 10 μM |
| 58 | H | CHCH | OMe | H | H | OMe | 49% @ 10 μM | 25% @ 10 μM |
| 59 | F | $CH_2$ | OMe | H | H | H | 1.17 | 4.51 |

Example 3

Central Nervous System (CNS) Permeation of the Compounds of the Invention Using Parallel Artificial Membranes (PAMPA)

The prediction of central nervous system (CNS) permeation of the various compounds, passage of the blood-brain barrier, was determined using parallel artificial membrane (PAMPA) methodology [Di, L.; Kems, E. H.; Fan, K.; McConnell, O. J.; Carter, G. T. "High throughput artificial membrane permeability assay for blood-brain barrier" *Eur. J. Med. Chem.*, 2003, 38 (3), 223-232]. To filter the samples, PVDF membrane filters (diameter: 30 mm, pore size: 0.45 μm) were used.

Ten reference compounds were selected, whose blood-brain barrier passage is known and public, in order to validate the experiment. Different quantities of the same 3-5 mg of caffeine, enoxacin, hydrocortisone, desipramine, ofloxacin, piroxicam and testosterone, 12 mg of promazine and 25 mg of verapamil and atenolol were taken, which were dissolved in ethanol (1000 μL). 100 μL of these solutions were taken and ethanol 1,400 μL of ethanol and 3,500 μL of PBS (pH=7.4) were added in order to reach a final concentration of 30% ethanol solution. The solutions were filtered. Next, 180 μL of a PBS/ethanol (70/30) solution were added to each well of the acceptor plate. The donor plate was impregnated with 4 μL of a porcine brain lipid solution dissolved in dodecane (20 mg $mL^{-1}$). After 5 min, 180 μL of dissolution of each compound were added to this plate. Of the compounds whose penetration into the central nervous system was to be assessed, between 1-2 mg were taken and dissolved in 1,500 μL of ethanol and 3,500 μL of PBS (pH=7.4), filtered and added to the donor 96-well plate. The donor plate was then placed on the acceptor forming a kind of "sandwich" and allowed to incubate for 2 hours and 30 min at 25° C. The compounds, by passive transport, will move from the donor plate through the porcine brain lipid to the acceptor plate. After 2 hours and 30 min, it was carefully removed from the donor plate. The concentration and absorbance, both of the commercial compounds and the synthesised derivatives evaluated in the acceptor and donor plates were determined using a UV absorbance reader. Each sample was analysed at different wavelengths (3 to 5) in three wells and in at least two independent experiments. The results are the average of the measurements [±standard deviation] of the different experiments performed.

In relation to the ten reference commercial compounds used in each experiment to validate the method, a good correlation between the experimental (Pe) and described permeation values, Pe (exptl)=1.1512 (bibl)−0.8973 ($R^2$=0.977) was found. Based on this equation and following the pattern described in the literature [Crivori, P.; Cruciani, G.; Testa, B. "Predicting Blood-Brain Barrier Permeation from Three-Dimensional Molecular Structure." *J. Med. Chem.*, 2000, 43, 2204-2216] for the prediction of permeation of the blood-brain barrier, the compounds can be classified as permeable to the central nervous system (CNS) when having a permeability >3.71×$10^{-6}$ $cm^{-1}$. The results are shown in Table 2, where it can be observed how some of the compounds tested are capable of penetrating the blood-brain barrier.

TABLE 2

PAMPA-blood-brain barrier permeation (Pe $10^{-6}$ cm $s^{-1}$) of ten compounds used to validate the experiment, and different compounds of the intervention with its corresponding predictionof penetration into the central nervous system (SNC).

| Compound | [a]Bibl. | [b]Pe ($10^{-6}$ cm $s^{-1}$) | Permeation prediction |
|---|---|---|---|
| Atenolol | 0.8 | 0.2 ± 0.1 | |
| Caffeine | 1.3 | 0.8 ± 0.1 | |
| Desipramine | 12 | 8.0 ± 1.0 | |
| Enoxacin | 0.9 | 0.7 ± 0.2 | |
| Hydrocortisone | 1.9 | 0.3 ± 0.3 | |
| Ofloxacin | 0.8 | 0.2 ± 0.1 | |
| Piroxicam | 2.5 | 0.2 ± 0.1 | |
| Promazine | 8.8 | 8.5 ± 0.1 | |
| Testosterone | 17 | 17.2 ± 0.6 | |
| Verapamil | 16 | 14.7 ± 1.1 | |
| 1 | | 9.6 ± 0.1 | SNC+ |
| 3 | | 14.6 ± 0.1 | SNC+ |

TABLE 2-continued

PAMPA-blood-brain barrier permeation (Pe $10^{-6}$ cm s$^{-1}$) of ten compounds used to validate the experiment, and different compounds of the intervention with its corresponding predictionof penetration into the central nervous system (SNC).

| Compound | [a]Bibl. | [b]Pe ($10^{-6}$ cm s$^{-1}$) | Permeation prediction |
|---|---|---|---|
| 4 | | 5.9 ± 0.5 | SNC+ |
| 5 | | 5.6 ± 0.8 | SNC+ |
| 6 | | 11.2 ± 2.0 | SNC+ |
| 8 | | 11.3 ± 2.1 | SNC+ |
| 10 | | 10.6 ± 0.1 | SNC+ |
| 12 | | 10.4 ± 3.9 | SNC+ |
| 14 | | 12.7 ± 1.2 | SNC+ |
| 20 | | 10.6 ± 0.3 | SNC+ |
| 30 | | 6.2 ± 0.5 | SNC+ |
| 51 | | 11.2 ± 0.9 | SNC+ |

[a]Di et al, 2003.
[b]Average data ± standard deviation of at least two independent experiments.

The invention claimed is:

1. A method of inhibiting the CK-1 enzyme comprising administering to a person in need thereof a compound of formula (I'):

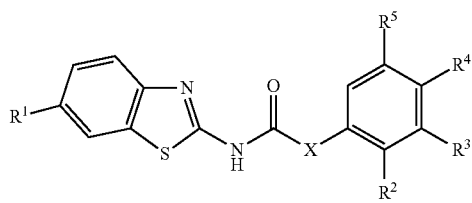

its pharmaceutically acceptable salts and/or tautomers, wherein

X is selected from among NH, CH$_2$, CHPh, CH$_2$CH$_2$, CH$_2$CHPh, CH=CH, CH$_2$OCH$_2$, CH$_2$NHCO, CH$_2$NHCOCHPh and CH$_2$NHCOCH$_2$, R$^1$ is CF$_3$, R$^2$, R$^3$, R$^4$ and R$^5$ are independently selected from among H, halogen and O-alkyl (C$_1$-C$_5$), provided that:

when X is CHPh, CH$_2$CHPh or CH$_2$NHCOCHPh, then R$^2$, R$^3$, R$^4$ and R$^5$ are H when R$^3$ and R$^4$ are both O-alkyl (C$_1$-C$_5$), then R$^5$ is O-alkyl (C$_1$-C$_5$); and wherein the person in need thereof comprises a person having a disease mediated by the CK-1 enzyme, and wherein the disease is selected from among acute neurological disorder, bipolar disorders and behavioural disorders, anxiety, depression, Alzheimer's disease, Parkinson's disease, postencephalitic Parkinsonism, Tourette syndrome, periodic limb movement pathologies, restless legs syndrome, Huntington's disease, progressive supranuclear palsy, Pick's disease, frontotemporal dementia, amyotrophic lateral sclerosis, muscular dystrophy, myotonic dystrophy and distal muscular dystrophy, cerebral palsy, Friedreich's ataxia, congenital myasthenic syndrome or myasthenia gravis.

2. The method according to claim 1, wherein X is CH$_2$, CH$_2$CH$_2$, CHPh or NH.

3. The method according to claim 2, wherein X is CH$_2$.

4. The method according to claim 1, wherein X is CH$_2$ and R$^1$ is CF$_3$.

5. The method according to claim 1, wherein said compound is selected from the following group:

N-(6-trifluoromethylbenzothiazole-2-yl)-2-(4-chlorophenyl)acetamide
N-(6-trifluoromethylbenzothiazole-2-yl)-2-(4-methoxyphenyl)acetamide
N-(6-trifluoromethylbenzothiazole-2-yl)-2-(3-chlorophenyl)acetamide
N-(6-trifluoromethylbenzothiazole-2-yl)-2-(3-methoxyphenyl)acetamide
N-(6-trifluoromethylbenzothiazole-2-yl)-2-(2-chlorophenyl)acetamide
N-(6-trifluoromethylbenzothiazole-2-yl)-2-(2-methoxyphenyl)acetamide
N-(6-trifluoromethylbenzothiazole-2-yl)-2-(3,4,5-trimethoxyphenyl)acetamide
N-(6-trifluoromethylbenzothiazole-2-yl)-2-phenylacetamide
N-(6-trifluoromethylbenzothiazole-2-yl)-2,2-diphenylacetamide
N-(6-trifluoromethylbenzothiazole-2-yl)-N'-(3-chlorophenyl)urea
N-(6-trifluoromethylbenzothiazole-2-yl)-2-(2,5-dimethoxyphenyl)acetamide
N-(6-trifluoromethylbenzothiazole-2-yl)-N'-(4-methoxyphenyl)urea
N-(6-trifluoromethoxybenzothiazole-2-yl)-2-(3,4,5-trimethoxyphenyl)acetamide and its pharmaceutically acceptable salts or tautomers.

6. The method according to claim 1, wherein the disease mediated by the CK-1 enzyme is selected from among depression and bipolar disorder.

7. The method according to claim 1, wherein the disease mediated by the CK-1 enzyme is selected from among Alzheimer's disease and frontotemporal dementia.

8. The method according to claim 1, wherein the disease mediated by the CK-1 enzyme is Parkinson's disease.

9. The method according to claim 1, wherein the disease mediated by the CK-1 enzyme is selected from among amyotrophic lateral sclerosis and frontotemporal dementia.

10. A compound of formula (I'):

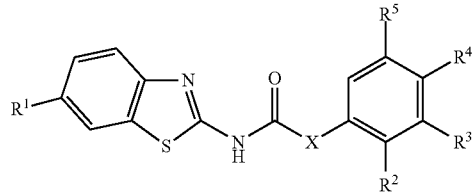

its pharmaceutically acceptable salts and/or tautomers, wherein

X is selected from among NH, CH$_2$, CHPh, CH$_2$CH$_2$, CH$_2$CHPh, CH=CH, CH$_2$OCH$_2$, CH$_2$NHCO, CH$_2$NHCOCHPh and CH$_2$NHCOCH$_2$, R$^1$ is CF$_3$, R$^2$, R$^3$, R$^4$ and R$^5$ are independently selected from among H, halogen and O-alkyl (C$_1$-C$_5$), provided that:

when X is CHPh, CH$_2$CHPh or CH$_2$NHCOCHPh, then R$^2$, R$^3$, R$^4$ and R$^5$ are H when R$^3$ and R$^4$ are both O-alkyl (C$_1$-C$_5$), then R$^5$ is O-alkyl (C$_1$-C$_5$).

11. A compound according to claim 10, wherein X is CH$_2$, CH$_2$CH$_2$, CHPh or NH.

12. A compound according to claim 11, wherein X is $CH_2$.

13. A compound according to claim 10, wherein X is $CH_2$ and $R^1$ is $CF_3$.

14. A compound according to claim 10, wherein said compound is selected from among the following group:
- N-(6-trifluoromethylbenzothiazole-2-yl)-2-(4-chlorophenyl)acetamide
- N-(6-trifluoromethylbenzothiazole-2-yl)-2-(2-chlorophenyl)acetamide
- N-(6-trifluoromethylbenzothiazole-2-yl)-2-(3-chlorophenyl)acetamide
- N-(6-trifluoromethylbenzothiazole-2-yl)-2-(4-methoxyphenyl)acetamide
- N-(6-trifluoromethylbenzothiazole-2-yl)-2-(3-methoxyphenyl)acetamide
- N-(6-trifluoromethylbenzothiazole-2-yl)-2-(2-methoxyphenyl)acetamide
- N-(6-trifluoromethylbenzothiazole-2-yl)-2-(3,4,5-trimethoxyphenyl)acetamide
- N-(6-trifluoromethylbenzothiazole-2-yl)-2-phenylacetamide
- N-(6-trifluoromethylbenzothiazole-2-yl)-2,2-diphenylacetamide
- N-(6-trifluoromethylbenzothiazole-2-yl)-N'-(3-chlorophenyl)urea
- N-(6-trifluoromethylbenzothiazole-2-yl)-2-(2,5-dimethoxyphenyl)acetamide
- N-(6-trifluoromethylbenzothiazole-2-yl)-N'-(4-methoxyphenyl)urea or its pharmaceutically acceptable salts or tautomers.

15. A compound according to claim 14, wherein said compound is selected from among the following group:
- N-(6-trifluoromethylbenzothiazole-2-yl)-2-(4-chlorophenyl)acetamide
- N-(6-trifluoromethylbenzothiazole-2-yl)-2-(2-chlorophenyl)acetamide
- N-(6-trifluoromethylbenzothiazole-2-yl)-2-(3-chlorophenyl)acetamide
- N-(6-trifluoromethoxybenzothiazole-2-yl)-2-(3,4,5-trimethoxyphenyl)acetamide
- N-(6-trifluoromethylbenzothiazole-2-yl)-2-(4-methoxyphenyl)acetamide
- N-(6-trifluoromethylbenzothiazole-2-yl)-2-(3-methoxyphenyl)acetamide
- N-(6-trifluoromethylbenzothiazole-2-yl)-2-(2-methoxyphenyl)acetamide
- N-(6-trifluoromethylbenzothiazole-2-yl)-2-(3,4,5-trimethoxyphenyl)acetamide
- N-(6-trifluoromethylbenzothiazole-2-yl)-2-phenylacetamide
- N-(6-trifluoromethylbenzothiazole-2-yl)-2,2-diphenylacetamide
- N-(6-trifluoromethylbenzothiazole-2-yl)-N'-(3-chlorophenyl)urea
- N-(6-trifluoromethylbenzothiazole-2-yl)-2-(2,5-dimethoxyphenyl)acetamide or its pharmaceutically acceptable salts or tautomers.

16. The compound of claim 15 wherein said compound is selected from among the following group:
- N-(6-trifluoromethylbenzothiazole-2-1)-2-(4-chlorophenyl)acetamide
- N-(6-trifluoromethylbenzothiazole-2-1)-2-(4-methoxyphenyl)acetamide
- N-(6-trifluoromethylbenzothiazole-2-1)-2-(3-chlorophenyl)acetamide
- N-(6-trifluoromethylbenzothiazole-2-1)-2-(3-methoxyphenyl)acetamide
- N-(6-trifluoromethylbenzothiazole-2-1)-2-(2-methoxyphenyl)acetamide
- N-(6-trifluoromethylbenzothiazole-2-1)-2-(3,4,5-trimethoxyphenyl)acetamide
- N-(6-trifluoromethylbenzothiazole-2-1)-2-phenylacetamide or its pharmaceutically acceptable salts or tautomers.

17. A pharmaceutical composition comprising a compound of formula (I'), as defined in claim 10.

18. A composition according to claim 17, further comprising another active ingredient.

19. A compound selected from:
- N-(6-trifluoromethoxybenzothiazole-2-yl)-2-(3,4,5-trimethoxyphenyl)acetamide
- N-(benzothiazole-2-yl)-2-(3-chlorophenyl)acetamide
- N-(6-methoxybenzothiazole-2-yl)-2-(3-chlorophenyl)acetamide
- N-(6-trifluoromethoxybenzothiazole-2-yl)-2-(3-chlorophenyl)acetamide
- N-(6-trifluoromethoxybenzothiazole-2-yl)-2-(3,4-dichlorophenyl)acetamide
- N-(benzothiazole-2-yl)-2-benzyloxyacetamide or its pharmaceutically acceptable salts or tautomers.

* * * * *

UNITED STATES PATENT AND TRADEMARK OFFICE
CERTIFICATE OF CORRECTION

PATENT NO. : 9,592,224 B2  
APPLICATION NO. : 14/762360  
DATED : March 14, 2017  
INVENTOR(S) : Martinez Gil et al.

It is certified that error appears in the above-identified patent and that said Letters Patent is hereby corrected as shown below:

On the Title Page

In Item [73], under Assignee, please delete "Donsejo" and insert --Consejo--.

Signed and Sealed this  
Eleventh Day of July, 2017

Joseph Matal  
*Performing the Functions and Duties of the*  
*Under Secretary of Commerce for Intellectual Property and*  
*Director of the United States Patent and Trademark Office*